(12) United States Patent
Cox

(10) Patent No.: US 11,486,799 B2
(45) Date of Patent: Nov. 1, 2022

(54) DEVICE FOR USE WITH MEASURING SOIL GAS AND METHOD OF USE

(71) Applicant: Vapor Pin Enterprises, Inc., Plain City, OH (US)

(72) Inventor: Craig A. Cox, Columbus, OH (US)

(73) Assignee: VAPOR PIN ENTERPRISES, INC., Plain City, OH (US)

( * ) Notice: Subject to any disclaimer, the term of this patent is extended or adjusted under 35 U.S.C. 154(b) by 761 days.

(21) Appl. No.: 16/381,525

(22) Filed: Apr. 11, 2019

(65) Prior Publication Data

US 2019/0323928 A1    Oct. 24, 2019

Related U.S. Application Data

(60) Provisional application No. 62/659,244, filed on Apr. 18, 2018.

(51) Int. Cl.
  *G01N 1/22*    (2006.01)
  *G01N 33/00*   (2006.01)
  *G01N 33/24*   (2006.01)

(52) U.S. Cl.
  CPC ....... *G01N 1/2294* (2013.01); *G01N 33/0047* (2013.01); *G01N 33/241* (2013.01)

(58) Field of Classification Search
  CPC ...... G01N 1/2294; G01N 33/241; G01N 1/10; G01N 1/2205; G01N 19/02; G01N 19/08; G01N 3/066; G01N 3/24; G01N 3/56; G01N 33/0047; Y10T 403/56; E21B 7/26
  See application file for complete search history.

(56) References Cited

U.S. PATENT DOCUMENTS

| | | |
|---|---|---|
| 2,141,261 A | 12/1938 | Clark |
| 3,343,421 A | 9/1967 | Miller |
| 3,379,461 A | 4/1968 | Davis |
| 3,490,288 A | 1/1970 | Patnode |
| 3,610,048 A | 10/1971 | Weeks |
| 3,711,130 A | 1/1973 | Betzler |
| 3,783,804 A | 1/1974 | Platz |
| 4,020,697 A | 5/1977 | Jander |

(Continued)

OTHER PUBLICATIONS

Shengtian Group: Advantages and Disadvantages of Threaded Fittings. Jul. 15, 2015 (Jul. 15, 2015). URL: http://www.stpipefitting.cn/company/news/198.html.

*Primary Examiner* — Nimeshkumar D Patel
*Assistant Examiner* — Gedeon M Kidanu
(74) *Attorney, Agent, or Firm* — Shumaker, Loop & Kendrick, LLP; James D. Miller

(57) ABSTRACT

Provided are installation devices and uses thereof for receiving and installing an adaptor body for sampling soil gas under a slab. The installation device includes a cylindrical body and an internal cavity. The cylindrical body has a length greater than a thickness of the slab, a first end configured to be placed adjacent a top of the slab, and a second end configured to be placed below a bottom of the slab. The internal cavity extends longitudinally through the cylindrical body from the first end to the second end, where the internal cavity has a first portion and a second portion. The first portion has a first diameter located at the first end of the cylindrical body and the second portion has a second diameter that is less than the first diameter. The internal cavity of the cylindrical body is configured to receive the adaptor body.

25 Claims, 22 Drawing Sheets

(56) References Cited

U.S. PATENT DOCUMENTS

| | | |
|---|---|---|
| 4,146,254 A | 3/1979 | Turner et al. |
| D254,505 S | 3/1980 | Parsons et al. |
| 4,261,203 A | 4/1981 | Snyder |
| 4,310,057 A | 1/1982 | Brame |
| 4,335,622 A | 6/1982 | Bartz |
| 4,350,051 A | 9/1982 | Thompson |
| 4,452,091 A | 6/1984 | Richers |
| 4,524,608 A | 6/1985 | Bellefeuille et al. |
| 4,603,890 A | 8/1986 | Huppee |
| 4,804,050 A | 2/1989 | Kerfoot |
| 4,807,707 A | 2/1989 | Handley et al. |
| 4,893,848 A | 1/1990 | Melcher |
| 4,951,976 A | 8/1990 | Boelkins |
| 4,969,879 A | 11/1990 | Lichte |
| 5,150,622 A | 9/1992 | Vollweiler |
| 5,176,411 A | 1/1993 | DuPont, Jr. |
| D333,178 S | 2/1993 | Novy |
| 5,330,235 A | 7/1994 | Wagner et al. |
| 5,403,046 A | 4/1995 | Kooten |
| D371,331 S | 7/1996 | Mooradian |
| 5,624,139 A | 4/1997 | Van Kooten |
| 5,711,551 A | 1/1998 | Miyazaki et al. |
| 5,786,527 A | 7/1998 | Tarte |
| 5,922,950 A | 7/1999 | Pemberton et al. |
| 6,152,495 A | 11/2000 | Hoffmann et al. |
| 6,230,820 B1 | 5/2001 | Cordry |
| 6,289,714 B1 | 9/2001 | Tartre |
| 7,281,439 B2 * | 10/2007 | Schmitt ............... G01N 1/2294 73/19.1 |
| 7,963,082 B1 * | 6/2011 | Bauer ............... E04G 23/0203 52/514 |
| 8,220,347 B2 * | 7/2012 | Cox ............... G01N 1/2294 73/866.5 |
| 10,012,571 B2 * | 7/2018 | Cox ............... G01N 1/2294 |
| 10,379,013 B2 * | 8/2019 | Cox ............... G01N 1/2294 |
| 10,921,222 B2 * | 2/2021 | Cox ............... G01N 1/2294 |
| 2001/0035057 A1 | 11/2001 | Jackson et al. |
| 2002/0043802 A1 | 4/2002 | Koster |
| 2003/0196498 A1 | 10/2003 | Hubbell et al. |
| 2004/0177672 A1 * | 9/2004 | Schmitt ............... G01N 1/2294 73/19.1 |
| 2006/0196114 A1 | 9/2006 | Allen |
| 2008/0028826 A1 * | 2/2008 | Schmitt ............... G01N 1/2294 73/19.01 |
| 2010/0112261 A1 | 5/2010 | Van Lumig et al. |
| 2011/0127767 A1 | 6/2011 | Wicks et al. |
| 2012/0000298 A1 * | 1/2012 | Cox ............... G01N 1/2294 73/864.73 |
| 2012/0282019 A1 * | 11/2012 | Cox ............... G01N 1/2294 403/299 |
| 2016/0153870 A1 * | 6/2016 | Cox ............... G01N 1/2294 73/864.73 |
| 2017/0356826 A1 * | 12/2017 | Cox ............... G01N 1/2294 |

* cited by examiner

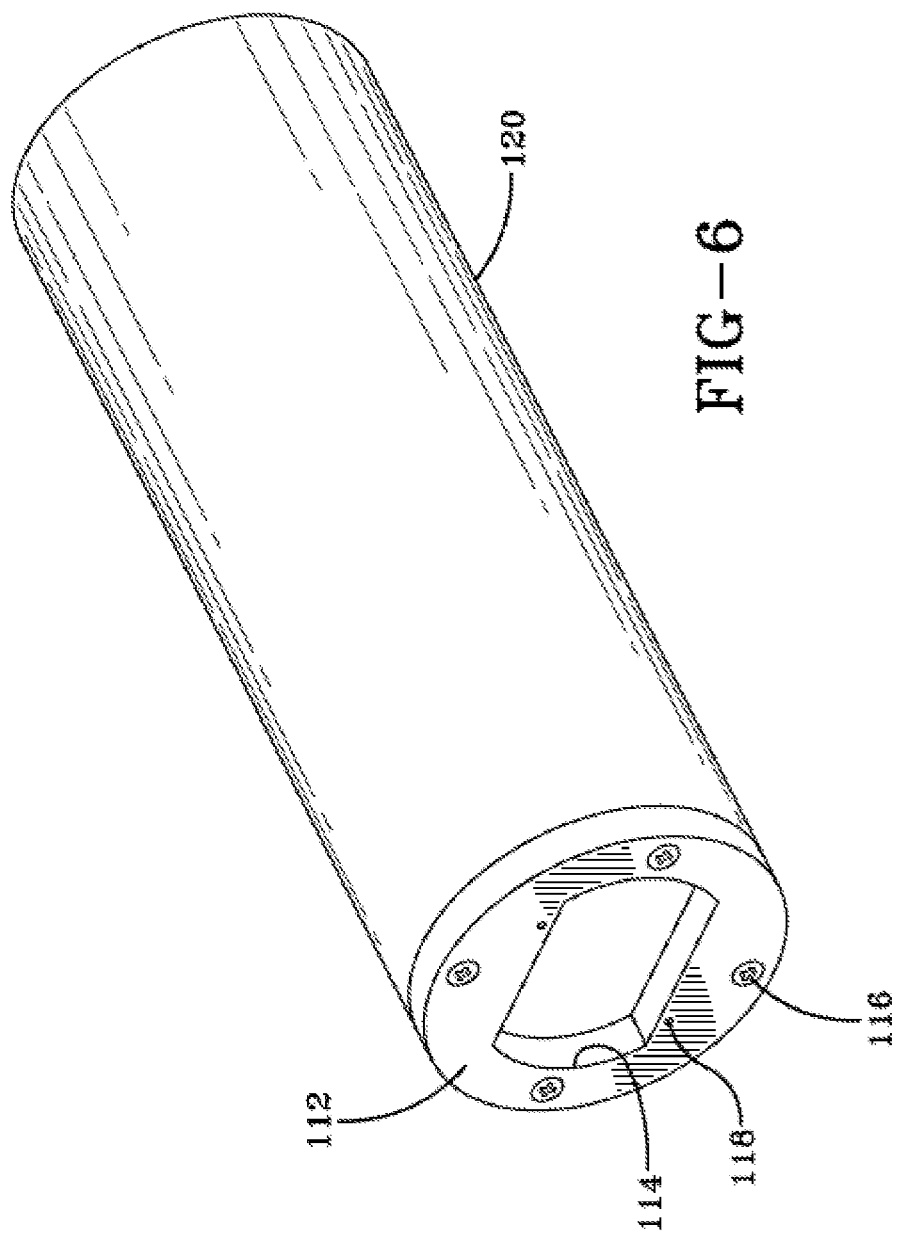

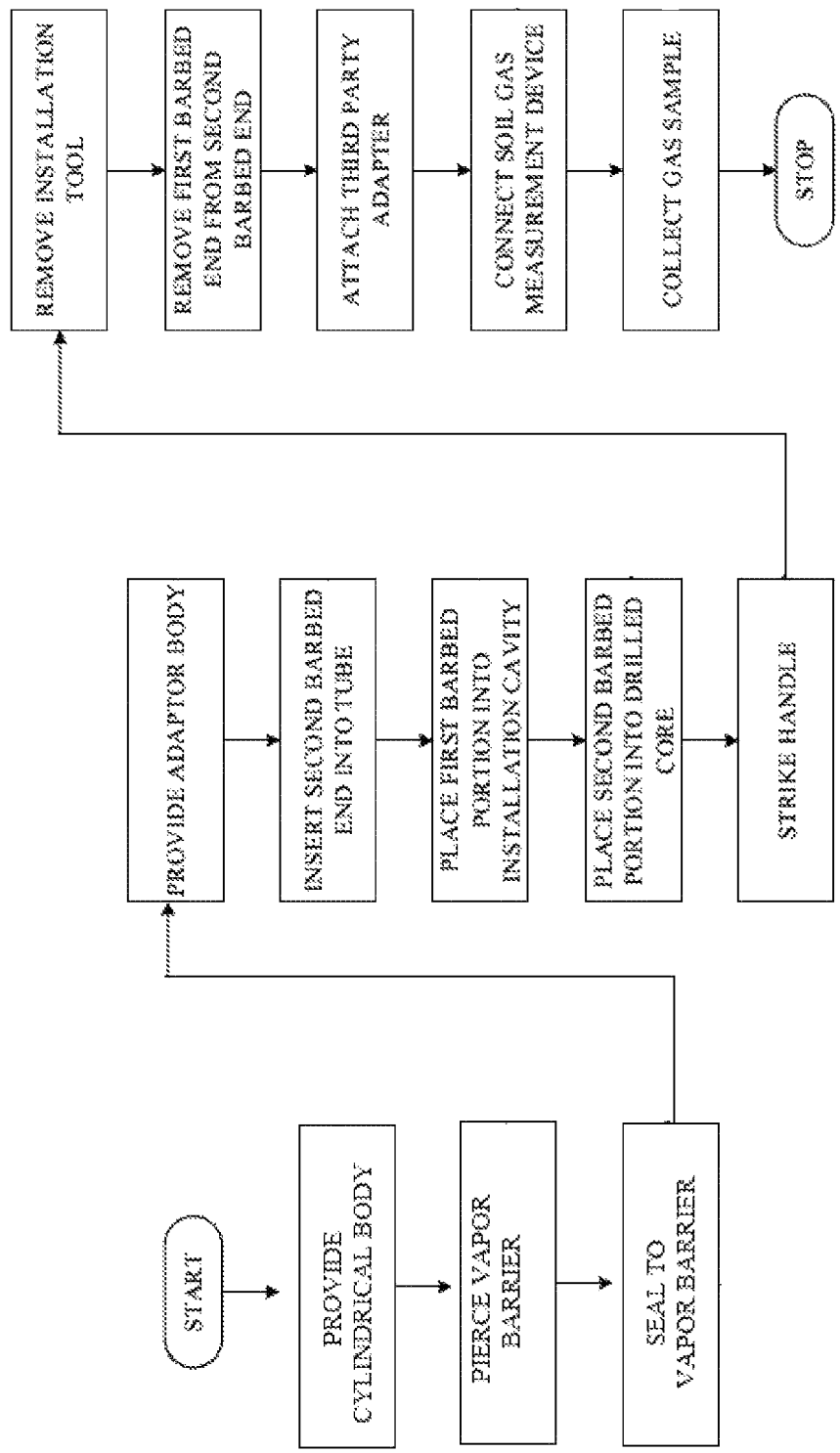

DEVICE FOR USE WITH MEASURING SOIL GAS AND METHOD OF USE

CROSS-REFERENCE TO RELATED APPLICATIONS

This application claims the benefit of U.S. Provisional Application No. 62/659,244, filed on Apr. 18, 2018. The entire disclosure of the above application is incorporated herein by reference.

FIELD

Exemplary embodiments are directed to mechanical devices and systems. More particularly, exemplary embodiments are directed to a device and system for facilitating the analysis of samples of sub-slab soil gas.

INTRODUCTION

This section provides background information related to the present disclosure which is not necessarily prior art.

The potential for volatile organic compounds (VOCs) associated with contaminated soil and groundwater to enter homes and businesses through basements and building slabs is a recent focus of federal and state environmental protections agencies. This potential route of exposure is commonly referred to as the "vapor intrusion pathway." Evaluations of the potential risk associated with long-term exposure to VOCs have been published by the United States Environmental Protection Agency (EPA) and other entities. These evaluations indicate that very low concentrations of some of these VOCs, on the order of a few parts per billion in some cases, can pose an unacceptable risk to building occupants. In some situations, sub-slab soil gas samples are collected to evaluate vapor concentrations and the potential for these vapors to enter a building.

The science of analyzing samples of sub-slab soil gas is known. However, the practicalities of collecting these samples of gas are quite cumbersome. Techniques and devices currently used and proposed in recent draft guidance documents by the EPA and other agencies to collect sub-slab soil gas samples are built upon the experience of environmental professionals gained over many years of sampling groundwater via monitor wells. In essence, the current state of the art for sub-slab sampling is the use of a miniature well installed through the slab. These wells, or "sub-slab vapor points" are typically installed by boring a fairly crude hole through the slab and cementing a metal tube in place. At the top of the tube are a number of threaded fittings that allow the vapor point to be connected via plastic tubing to an evacuated vessel, known in the art as a summa canister.

Because the levels of concern for many of the VOCs are so low, leaks in the vapor point fittings or along the edge of the vapor point itself allow indoor air to dilute the sample, rendering the sample useless. This situation is exacerbated by the fact that most vapor points must be sampled on multiple occasions. Each time the vapor point is used it must be disconnected and reconnected using multiple wrenches, usually in tight quarters. This activity can cause some fittings to progressively loosen and leak more readily, or result in the point itself losing its bond with the cement used to anchor it during installation. Federal and state EPA officials recognize this shortcoming and have developed elaborate, time consuming methods for detecting such leaks.

The collection of sub-slab samples can also be inconvenient to building occupants since it requires the removal of floor coverings and coring or drilling of the foundation slab. One recommended method is using an electric hammer drill or rotary hammer to produce an inner pilot hole into the concrete slab. After the pilot hole is drilled, an individual must drill an outer hole to a predetermined depth using a larger drill bit. After the outer hole is finished, the individual must use the original tool to assure that the pilot hole is then drilled through the slab and several inches into the sub-slab material. Once the drilling is completed, a stainless steel probe is assembled and inserted into the pre-drilled hole. The probe is mounted as flush as possible with the surrounding slab to minimize the interference with pedestrian or vehicular traffic. The probe has to be cemented into place to ensure that the probe assembly is air-tight with the foundation slab. Since the cement has to cure, an individual must come back at least one further time before sampling of the sub-soil may occur, further inconveniencing a homeowner or business.

Attempts have been made to overcome these and other difficulties inherent in the task of collecting sub-slab soil gas samples for analysis. Various devices and systems have been developed for use in such collection, for instance those previously described in U.S. Pat. No. 8,220,347 and U.S. patent application Ser. No. 13/551,213, both co-owned by the applicant and the fully incorporated herein by reference. Those references disclose invented devices, systems and their methods of use that facilitate the collection of sub-slab soil gas samples by, in part, eliminating the intrusion of the collection system on the interior building space, reducing the potential for damage to the slab introduced by previously used methods of collection, reducing or eliminating the risk of leakage during sampling thereby increasing testing efficacy/efficiency, and reducing collection costs through the introduction of reusable system components, for instance.

However, it has been found that certain disadvantages and drawbacks remain in the current state-of-the-art devices and systems. For example, variations in slab, bedding and foundation thicknesses, and in geographic structures of various testing locations have resulted in a need for sub-slab soil gas collection at variable depths relative to the top surface of a particular slab. Furthermore, as the art of sub-slab soil gas analysis continues to advance, soil gas collection may be needed at an increasing variety of depths relative to the top surface of a given slab. In some instances, drilling well into the backfill or native material beneath a slab to a desired depth for collection is found to increase the potential for clogging or the introduction of undesirable particulates into the vapor stream entering the sampling device.

In some cases, it may be desirable to introduce an external sampling device or probe into a space beneath a slab. Currently known sampling systems, however, either are not compatible with such sampling devices or require invasive installation techniques that are cumbersome, undesirable, and often cause unwanted damage to the slab or structure.

What is desired are devices and systems that eliminate some or all of the drawbacks of the known devices and techniques for measuring sub-slab soil gas. Providing a leak-resistant device that allows for prompt installation and removal, saving time and money may eliminate some or all of these drawbacks. Also, a device and system that allows for installation to occur in one appointment is desirable. Such a device may also be designed for use with different VOC measuring devices, both above- and below-slab, and with other sampling devices generally. There is also need for a system that provides some or all of these advantages in addition to the ability to collect samples at a point beneath the slab, and without clogging or contamination of the device and sample, respectively. No known references, taken alone or in combination, are seen as teaching or suggesting the presently claimed apparatus for use in the sampling of sub-slab soil gas.

SUMMARY

Exemplary embodiments of the device may eliminate some or all of the aforementioned drawbacks of the current art. Exemplary embodiments of the system components may be machined from a single piece material, such as brass or stainless steel, eliminating the need for multiple fittings and thereby reducing the number of potential leaks. Exemplary embodiments of the system may be installed into a one-inch diameter hole cored through the slab of concrete or other foundation material. The cored hole provides a smoother bonding surface and can be accomplished using a standard, hand-held coring machine. Exemplary embodiments of the system may be driven into the cored hole using a hammer or similar device. Installation of exemplary embodiments of the system forces flexible silicone tubing located on at least a portion of the exterior surface of an adaptor body against the interior wall of the cored hole, effectuating an air-tight, or almost air-tight, seal between the cored slab and the device. Exemplary embodiments of the adaptor body of the system may then be connected to a portion of sampling tubing via an air-tight barbed fitting.

Exemplary embodiments of the system include an adaptor body having a length and proximal and distal ends. The adaptor body includes a first barbed portion disposed at the proximal end of the adaptor body, a second barbed portion disposed at the distal end of the adaptor body, a collar portion disposed between the first and second barbed portions, an internal cavity having an interior surface and passing through the length of the adaptor body, and a coupling portion having an internal thread disposed on the interior surface of the internal cavity and extending longitudinally thereon from the distal end of the adaptor body.

On object of the innovation is to provide a system that can be used to collect sub-slab soil gas at varying depths with respect to the top surface of a given slab, without necessitating the manufacture of adaptor body components having many different lengths. Another object of the innovation is to provide a system that can be used to collect sub-slab soil gas at points beneath the give slab without introducing particulates into the vapor stream being collected, and without increasing the potential for clogging occurring in the cavities of the system. Exemplary embodiments of such a system include an extension having a length a first and second ends. The extension has an internal cavity extending longitudinally through the extension from the first end of the extension to an outlet at the second end of the extension, and an external thread disposed at the first end of the extension adapted for complimentary threaded retention within the coupling portion of the adaptor body.

In some embodiments, the extension is a fitting extension having a fitting portion disposed at the outlet. The fitting extension may be, for instance a barbed portion disposed at the outlet, wherein one or more generally frustum shaped barbs are disposed thereon whereby other down-hole sampling devices may be attached to the system directly or indirectly, for instance via stainless steel or rigid or flexible plastic tubing. Some exemplary embodiments include an external engaging portion disposed between the external thread and the barbed portion of the fitting extension. The external engaging portion may have a lateral cross-sectional shape adapted for use with a tool such as a wrench to tighten or loosen the connection between the extension and the adaptor body.

In some exemplary embodiments of the system, the extension is a filter extension having a filter element disposed at the outlet. The filter element may, for instance, include a filter element having an attachment aperture and at least one internal rib disposed within the attachment aperture, and a barbed portion having at least one barb disposed at the outlet, wherein the barbed portion is retained within the attachment aperture of the filter element by complimentary engagement between the at least one internal rib and the at least one barb. In some embodiments, the filter element is formed of a sintered porous metal. Exemplary embodiments of the system may include a filter extension having an external engaging portion disposed between the external thread and the barbed portion of the filter extension. The external engaging portion may, for instance, have a lateral cross-sectional shape adapted for use with a tool such as a wrench to tighten or loosen the connection between the filter extension and the adaptor body.

Further exemplary embodiments of the system may be provided wherein the extension is a sieve extension having a plurality of lateral outlets wherein each lateral outlet intersects with the internal cavity of the sieve extension. In some embodiments, the sieve extension may include an external engaging portion disposed at its second end. The external engaging portion may, for instance, have a lateral cross-sectional shape adapted for use with a tool such as a wrench to tighten or loosen the connection between the sieve extension and the adaptor body. In some embodiments, the external engaging portion has a length and a circular cross-sectional shape with two opposing parallel sides. One object of the system is to provide lateral gas passageways by way of a plurality of lateral outlets. In some embodiments, the plurality of lateral outlets has at least one pair of outlet cavities extending laterally through the engaging portion in an intersecting "X" pattern. In preferred embodiments, the lateral outlets are provided as three pair of outlet cavities extending laterally through the engaging portion, wherein each pair is configured in an intersecting "X" pattern.

Another object of the present innovation is to provide a system for sampling sub-slab soil gas wherein the outlet or outlet(s) may be positioned at variable depths and even beneath a slab. A further object is to provide such ability without requiring the manufacture of a wide variety of adaptor bodies having differing lengths. In some embodiments, the adaptor body and extension are further provided with a length extension having first and second ends coupled to and between the adaptor body and extension. The length extension has an internal cavity having an interior surface extending longitudinally through the length extension from the first end to the second end, an external thread disposed at the first end adapted for complimentary threaded retention within the coupling portion of the adaptor body, and a coupling portion having an internal thread disposed on the interior surface and extending longitudinally thereon from the second end of the length extension, wherein the internal thread is adapted to threadably retain the external thread of the extension. The installation of an embodiment of the invented system having an adaptor body, length extension and extension such as a fitting extension, filter extension or sieve extension, for instance, allows for the collection of soil gas samples via a continuous internal cavity having one or more outlets wherein the soil gas may enter and travel to the proximal end of the adaptor body for analysis.

An exemplary embodiment of the device may be associated with an automated installation device. Such a device may be robotic in nature, or may be another type of automated device. Alternatively, an exemplary embodiment of the device may be employed by an individual to manually install the device, such as by a hammer.

It is an object of this innovation to provide a system for use in the collection of sub-slab soil gas of the type generally described herein, being adapted for the purposes set forth herein, and overcoming disadvantages found in the prior art. These and other advantages are provided by the innovation described and shown in more detail below.

In another aspect of the innovation, a soil gas collecting device is disclosed that includes a first body portion having a first barbed end and a male connection mechanism, a second body portion having a second barbed end and a first female receiving mechanism that receives the male connection mechanism, a grip portion that facilitates the attachment and removal of the first body portion from the second body portion, and an internal cavity axially extending the length of both the first body portion and the second body portion that allows soil gas to flow through the first body portion and the second body portion.

In another aspect of the innovation, the second body portion includes a threaded collar disposed at a first end of the second barbed end portion that facilitates the installation and removal of the device, the threaded collar including at least one thread having oppositely disposed flat surfaces that facilitates prevention of rotation of the second body portion after installation.

In another aspect of the innovation, the second body portion includes a smooth collar disposed at a first end of the second barbed end portion that facilitates the installation of the device. The smooth collar may further include oppositely disposed flat surfaces to facilitate the prevention of rotation of the second body portion after installation. The second body portion includes no more than two barbs, which facilitate the installation of the device in thin slabs. The barbs may be surrounded by a sleeve to create a seal between the device and the slab.

In another aspect of the innovation, the second body portion includes a projection portion disposed at a second end of the second barbed end and including a second female receiving mechanism that receives an extension. The projection portion includes a first cylindrically shaped projection and a second cylindrically shaped projection having a diameter that is larger than a diameter of the first cylindrical projection, and wherein the second cylindrically shaped projection includes a beveled edge that facilitates installation.

In another aspect of the innovation, a soil-gas collecting device is disclosed that includes a cylindrical body having a length and first and second ends, comprising: an internal cavity having an interior surface and passing through the length of the cylindrical body; and a collar portion disposed between the first end and the second end of the cylindrical body. The collar portion including a first cylindrical shaped projection and a second cylindrical shaped projection having a diameter that is smaller than the diameter of the first cylindrical projection. The second end of the cylindrical body facilitates the piercing of and the sealing to a vapor barrier. The internal cavity extending the length of the cylindrical body allows soil gas to flow from underneath the vapor barrier through the internal cavity. The collar portion of the cylindrical body is adapted to allow the installation of an adaptor body. The adaptor body includes a length and proximal and distal ends and comprising: a first barbed portion disposed at the proximal end of the adaptor body; a second barbed portion disposed at the distal end of the adaptor body. A collar portion is disposed between the first barbed portion and the second barbed portion. The adaptor body also includes an internal cavity having an interior surface and passing through the length of the adaptor body; and a coupling portion comprising an internal thread disposed on the interior surface and extending longitudinally thereon from the distal end of the adaptor body. In addition to gas collection, the cylindrical body facilitates the collection of sub-slab pressure readings.

Yet another aspect of the innovation includes an installation device for receiving and installing an adaptor body for sampling soil gas under a slab, where the slab has a thickness defined by a top and a bottom thereof. The installation device can include a cylindrical body and an internal cavity. The cylindrical body can have a length greater than the thickness of the slab, where a first end is configured to be placed adjacent the top of the slab and a second end is configured to be placed below the bottom of the slab. The internal cavity can extend longitudinally through the cylindrical body from the first end of the cylindrical body to the second end of the cylindrical body, where the internal cavity has a first portion and a second portion. The first portion can have a first diameter located at the first end of the cylindrical body and the second portion can have a second diameter that is less than the first diameter. The internal cavity of the cylindrical body can be configured to receive the adaptor body therein.

A further aspect of the innovation includes where the installation device can include an adaptor body having a length, a proximal end, and a distal end. The adaptor body can also include a first barbed portion disposed at the proximal end of the adaptor body and a second barbed portion disposed at the distal end of the adaptor body. A collar portion can be disposed between the first barbed portion and the second barbed portion. And the adaptor body can have an internal cavity having an interior surface, where the internal cavity passes through the length of the adaptor body. The adaptor body can be disposed within the installation device. For example, the first barbed portion of the adaptor body can be located within the first portion of the internal cavity of the installation device and the second barbed portion of the adaptor body can be located within the second portion of the internal cavity of the installation device.

Methods of installing an installation device are provided where a rod can be placed into a sub-slab base material, the rod having a length greater than the cylindrical body of the installation device, and the rod configured to be disposed through the internal cavity of the cylindrical body. The cylindrical body of the installation device can be disposed about the rod, the rod can be disposed through the internal cavity of the cylindrical body, and the second end of the cylindrical body can be disposed into the sub-slab base material. The rod can then be removed from the sub-slab base material and the cylindrical body of the installation device.

Method of collecting a gas sample are provided that include drawing a gas sample through an adaptor body from a sub-slab base material. The adaptor body can be disposed within an installation device, the installation device can be disposed within a slab, and the slab can have a thickness defined by a top and a bottom thereof.

DRAWINGS

The drawings described herein are for illustrative purposes only of selected embodiments and not all possible implementations, and are not intended to limit the scope of the present disclosure. In addition to the features mentioned above, other aspects of the present invention will be readily apparent from the following descriptions of the drawings and exemplary embodiments, wherein like reference numerals across the several views refer to identical or equivalent features, and wherein:

FIG. 6 is a perspective view of an exemplary embodiment of an installation tool in accordance with an aspect of the innovation;

FIG. 27 is a flow chart diagraming a method of collecting gas samples in accordance with an aspect of the innovation.

DETAILED DESCRIPTION

Figure 1:
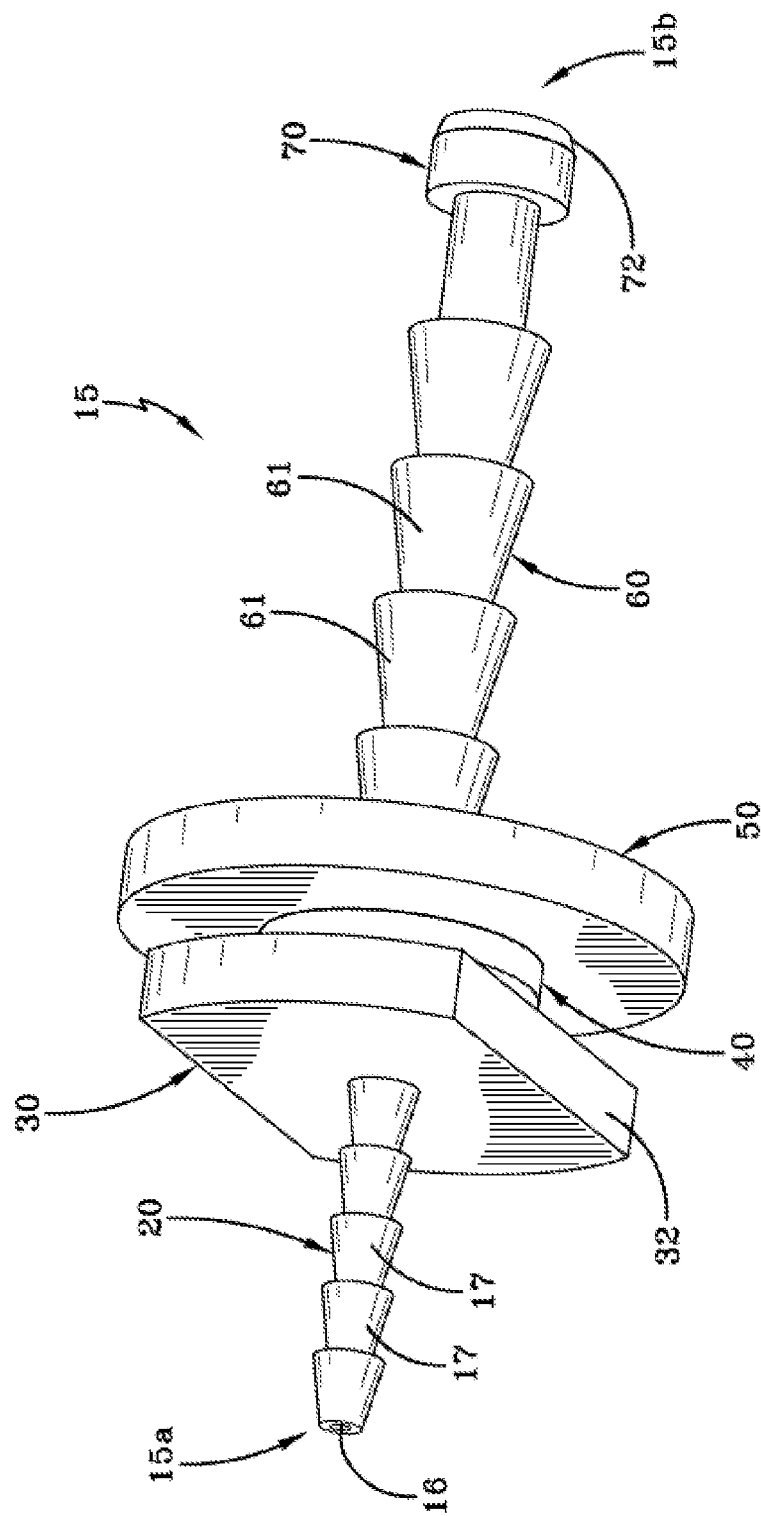
FIG. 1 is a perspective view illustrating an exemplary embodiment of an adaptor body in accordance with an aspect of the innovation.

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. Regarding methods disclosed, the order of the steps presented is exemplary in nature, and thus, the order of the steps can be different in various embodiments. "A" and "an" as used herein indicate "at least one" of the item is present; a plurality of such items may be present, when possible. Except where otherwise expressly indicated, all numerical quantities in this description are to be understood as modified by the word "about" and all geometric and spatial descriptors are to be understood as modified by the word "substantially" in describing the broadest scope of the technology. "About" when applied to numerical values indicates that the calculation or the measurement allows some slight imprecision in the value (with some approach to exactness in the value; approximately or reasonably close to the value; nearly). If, for some reason, the imprecision provided by "about" and/or "substantially" is not otherwise understood in the art with this ordinary meaning, then "about" and/or "substantially" as used herein indicates at least variations that may arise from ordinary methods of measuring or using such parameters.

All documents, including patents, patent applications, and scientific literature cited in this detailed description are incorporated herein by reference, unless otherwise expressly indicated. Where any conflict or ambiguity may exist between a document incorporated by reference and this detailed description, the present detailed description controls.

Although the open-ended term "comprising," as a synonym of non-restrictive terms such as including, containing, or having, is used herein to describe and claim embodiments of the present technology, embodiments may alternatively be described using more limiting terms such as "consisting of" or "consisting essentially of." Thus, for any given embodiment reciting materials, components, or process steps, the present technology also specifically includes embodiments consisting of, or consisting essentially of, such materials, components, or process steps excluding additional materials, components or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein.

As referred to herein, disclosures of ranges are, unless specified otherwise, inclusive of endpoints and include all distinct values and further divided ranges within the entire range. Thus, for example, a range of "from A to B" or "from about A to about B" is inclusive of A and of B. Disclosure of values and ranges of values for specific parameters (such as amounts, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that Parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if Parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, 3-9, and so on.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

A portion of the following detailed description first discusses prior art devices known for use in sub-slab soil gas analysis, taken and adapted in part from U.S. Pat. Nos. 8,220,347 and 9,291,531, both co-owned by the applicant. Reference should be made therein for further details regarding the current state of the art. FIG. 1 depicts one exemplary embodiment of a known prior art adaptor body. As shown, this particular adaptor body 15 includes a first barbed portion 20, an external engaging portion 30, a recess 40, a collar portion 50, a second barbed portion 60 and a raised end 70.

Figure 2B:
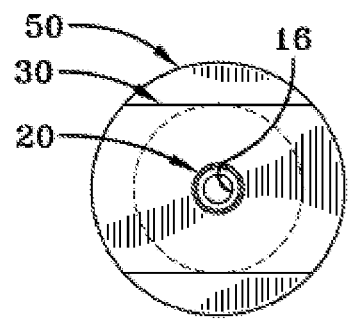
FIG. 2b is a top plan view thereof in accordance with an aspect of the innovation.
Figure 2A:
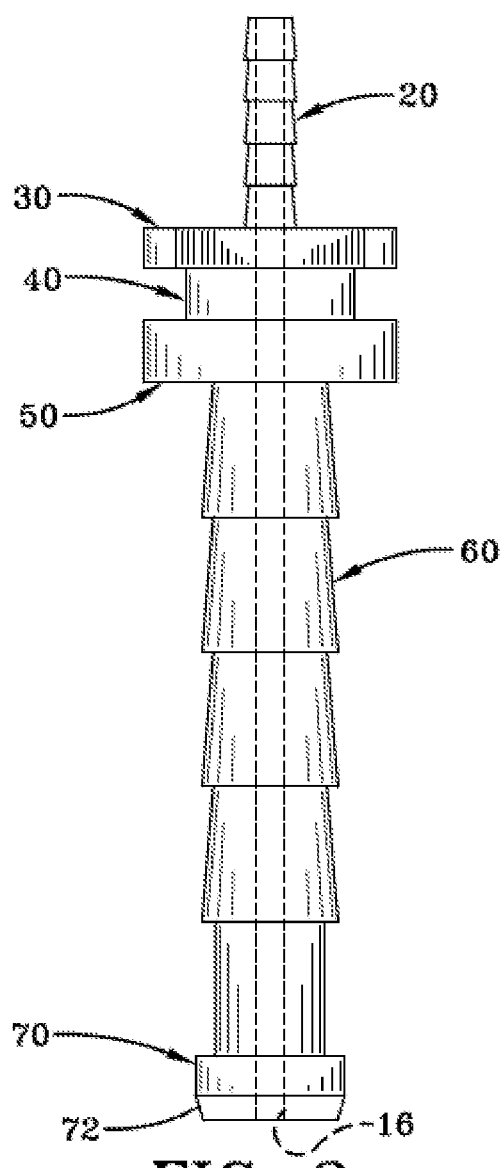
FIG. 2a is a front elevation view thereof in accordance with an aspect of the innovation.

As shown in FIGS. 1-2b, the adaptor body includes a proximal end 15a and a distal end 15b. Exemplary embodiments of the adaptor body 15 may include a first barbed portion 20, an external engaging portion 30, a recess 40, a collar portion 50, a second barbed portion 60 and a raised end 70. As seen in FIGS. 2a-2b, adaptor bodies 15 are known to include an internal cavity 16 that axially passes through the length of the adaptor body 15 from the proximal end 15a to the distal end 15b. The internal cavity 16 allows gas found in the subsoil to flow through the adaptor body 15 and be read by a soil gas measuring device (not shown) that is connected with the adaptor body 15. The cross-sectional area and geometry of the internal cavity 16 may be substantially similar throughout the length of the adaptor body 15.

In this embodiment, the first barbed portion 20 of the adaptor body 15 is located towards the proximal end 15a thereof. The first barbed portion 20 generally includes at least one barb 17. In some examples, the barbs 17 are generally conical in geometry to facilitate the releasable securement of an exemplary embodiment of tubing (not shown) that connects the adaptor body 15 with a soil gas measuring device, such as a SUMMA canister. As such, the first barbed portion 20 is often manufactured from readily available sizes of round stock, thereby reducing manufacturing time and expense, although it may have any number of cross-sectional geometries depending upon the cross-sectional geometry of the tubing that connects the device with the soil gas measuring device. Typically, the end-most barb located towards the proximal end 15a may include a generally rounded face that facilitates the insertion of the first barbed portion 20 within the inner cavity of the tubing that connects the adaptor body 15 with a soil gas measuring device. In some exemplary embodiments, there are no gaps or land sections between the barbs 17. In such embodiments, the end of the barb with the smaller outside diameter may abut the next barb's end with the larger outside diameter.

Figure 3B:
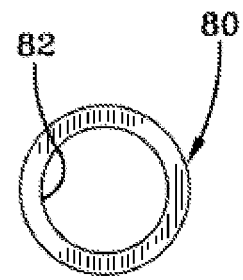
FIG. 3b is a top plan view thereof in accordance with an aspect of the innovation.
Figure 3A:
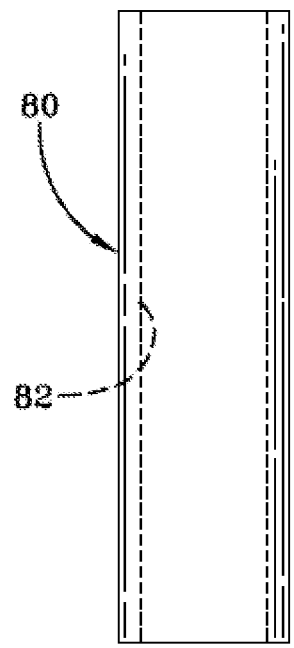
FIG. 3a is a front elevation view of an exemplary embodiment of a tubular body in accordance with an aspect of the innovation.

Typically, when the barbs 17 bear a fixed dimensional relationship to the inside diameter of the tubing that connects the adaptor body 15 with a soil gas measuring device, the tubing will form a reliable pressure tight seal to the adaptor body 15. In one embodiment, the large diameter ends of the barbs 17 may be approximately 0.30", while the inner diameter of the tubing may be approximately 0.25". This type of press-fit may cause the tube to spread or flare so that after the first barbed portion 20 is fully inserted within the tube, the tube will return to its original size after releasable securement. Furthermore, in some embodiments, the conical shape of the barb 17, which is wider toward the point of insertion, provides a manner of anchoring the flexible tubing body 80 during the insertion process so that the tubing body 80 does not move in relation to the adaptor body 15 during insertion (see FIGS. 3a and 3b).

The external engaging portion 30 of the adaptor body 15 includes an external engaging portion, in this example, a flange 32 adapted to engage a wrench or other tool. The external engaging portion 30 is shown here to be of substantially circular shape, wherein a portion of opposed sides are substantially parallel to one another. However, other shapes are also possible. In another example, the outside geometry of the external engaging portion 30 is substantially hexagonal or square in geometry to allow a user to engage thereto with a wrench or other tool. While this embodiment of the fastener engaging portion contains a flange, other embodiments are known to include a component, which allows for engagement with different tools, including a screwdriver head component, a hex head component, TORX head component, drill head component, or another engaging structure that can tighten and/or move the adaptor body 15 by rotational movement.

In some embodiments, the engaging portion 30 may be integral with the first barbed portion 20, such as by molding or turning. In other embodiments, the engaging portion 30 may be attached to the first barbed portion 20, such as by welding. Alternatively, the first barbed portion 20 may be removably attached to the engaging portion 30 so that the device 15 may be used with tubing of various sizes.

Figure 5A:
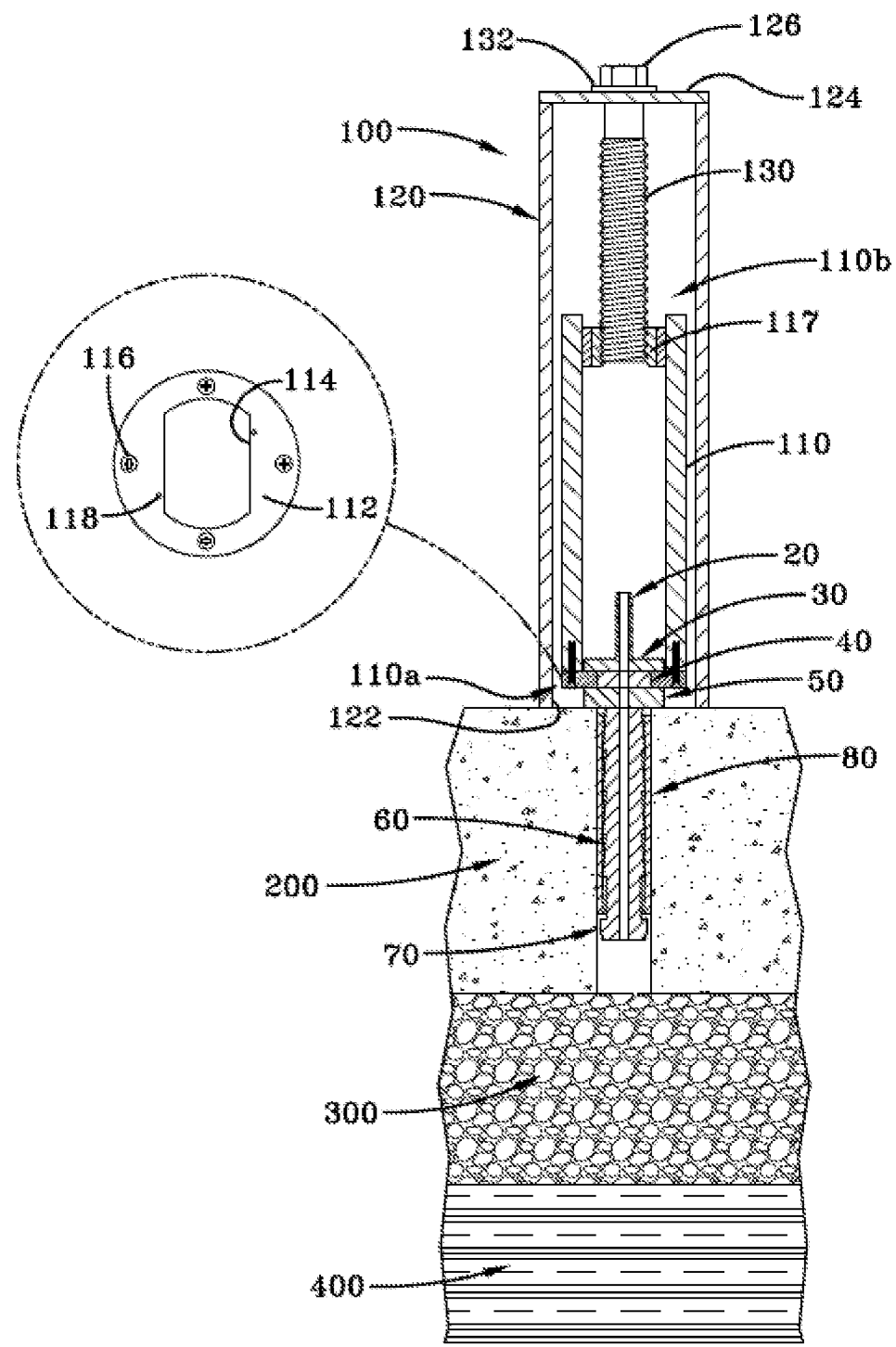
FIG. 5a is a sectional view of the adaptor body and tubular body of FIG. 4 with the installation tool prior to extraction in accordance with an aspect of the innovation.
Figure 5B:
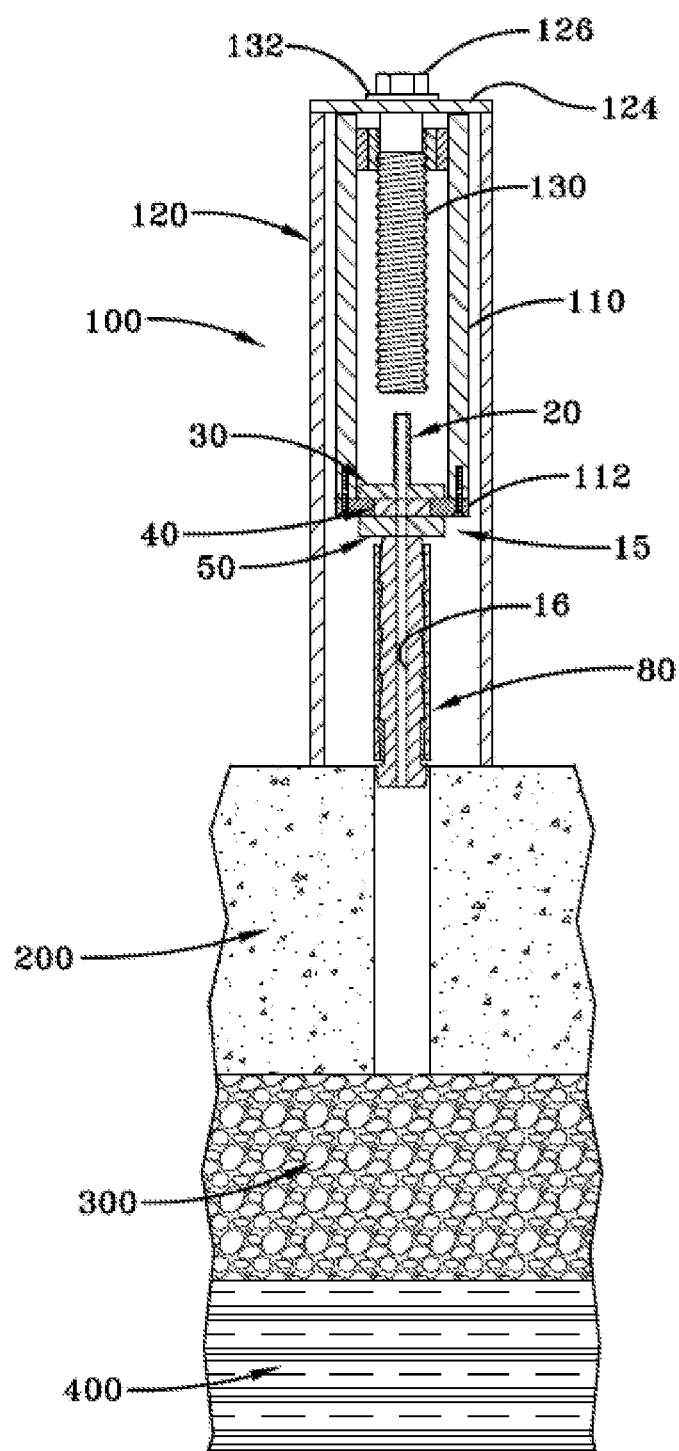
FIG. 5b is a sectional view thereof after extraction has occurred in accordance with an aspect of the innovation.

In exemplary embodiments, the collar portion 50 is generally joined to the engaging portion 30 by an optional recess area 40 which has a generally cylindrical shape. The geometry of the recess area 40 may be of various cross-sectional areas, although a substantially round cross-sectional area may simplify manufacturing. The optional recess area 40 may also allow a wrench or other tool 100 to engage the engaging portion 30 and/or the collar portion 50 of the adaptor body 15 to facilitate the installation and/or removal of the adaptor body 15. In one example, as seen in FIGS. 5a and 5b, an individual may use the tool 100 to install and/or remove the device.

Figure 4:
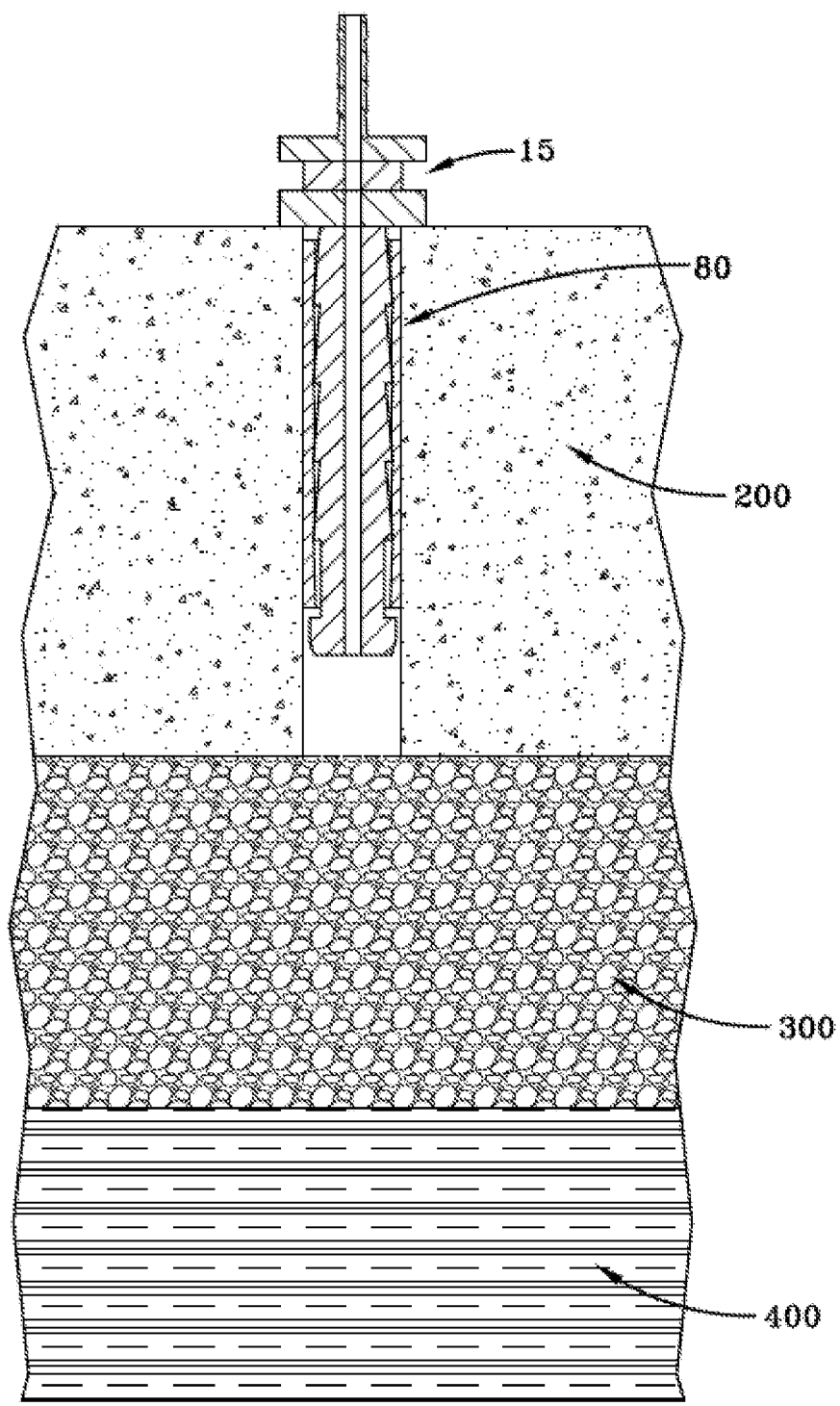
FIG. 4 is a sectional view of an exemplary embodiment of an adaptor body and tubular body installed within a foundation slab in accordance with an aspect of the innovation.

In this example, the entire collar portion 50 is substantially circular in cross-sectional geometry, wherein the diameter is substantially the same along the length thereof. The cross-sectional geometry of the collar section is typically substantially circular to facilitate the insertion of adaptor body 15 within in a corresponding hole in the slab that is likewise substantially circular. However, in other embodiments, the collar portion 50 may also be of other cross-sectional shapes. As aforementioned, one of the main functions of the collar portion 50 is to provide a surface for a tool to contact the adaptor body 15 for installation and/or removal of the adaptor body 15 during use. In some embodiments, during installation of the adaptor body 15, once the distal end of the collar portion 50 engages a portion of the slab, the device is fully engaged, as depicted in FIG. 4. In some embodiments, the collar portion 50 may taper inward (not shown) from a larger diameter as it extends longitudinally from the proximal end 15a of the adaptor body 15. The taper may facilitate the securement of the tubular body 80 to the adaptor body 15 during installation. In some embodiments, the collar portion 50 may be integral with the engaging portion 30, and the recess portion 40 such as by molding or turning. In other embodiments, the engaging portion 30 and the collar portion 50 may be attached to the recess portion 40, such as by welding.

As shown in the illustration of a known adaptor body as depicted in FIGS. 1-2b, the second barbed portion 60 of the adaptor body 15 may be located towards the distal end 15b thereof. The second barbed portion 60 generally includes at least one barb 61. In some examples, the barbs 61 are generally conical in geometry to facilitate the releasable securement of the tubing body 80, as seen in FIG. 4. As such, the second barbed portion 60 may be manufactured from readily available sizes of round stock, thereby reducing manufacturing time and expense. However, it should be realized that the second barbed portion 60 may have any number of cross-sectional geometries, depending upon the cross-sectional geometry of the tubular body 80. Typically, the barbs 61 may taper from a larger diameter from the distal end 15b thereof. However, in other embodiments, some or all of the barbs 61 may taper from a larger diameter from the proximal end 15a thereof. In some exemplary embodiments, there are no gaps or land sections between the barbs 61. In such embodiments, the end of the barb with the smaller outside diameter may abut the next barb's end with the larger outside diameter.

Typically, when the barbs 61 bear a fixed dimensional relationship to the inside diameter of the tubular body 80 there will form a reliable pressure tight seal therebetween. In one embodiment, the large diameter ends of the barbs 61 may be approximately 0.79", while the inner diameter of the tubular body 80 may be approximately 0.75". This type of press-fit may cause the tube to spread or flare so that after the second barbed portion 60 is fully inserted within the tubular body 80, the tubular body 80 will return to its original size after releasable securement.

The exemplary embodiment raised end 70 of FIG. 1 can be seen in more detail in FIG. 2a. As shown, the raised end 70 is a substantially cylindrical shape, although other shapes are possible. This example of the raised end include a chamfer 72 or rounded end located at the distal end 15b of the adaptor body 15, which facilitates the insertion of the raised end 70 within the inner cavity of the tubular body 80. Typically, but not necessarily, the outside diameter of the raised end 70 is approximately the same diameter of the largest diameter of the barbs 61. However, in other embodiments, the outside diameter of the raised end 70 may be greater or less than the outside diameter of the barbs 61.

Adaptor bodies may be made of any number of materials, such as, for example, brass, plastics, or other metals, such as stainless steel. Whatever material is selected, the resulting adaptor body 15 should have sufficient strength to withstand the insertion and extraction of the adaptor body within the slab. Furthermore, it is preferred that the material is easy to manufacture, if machined.

As shown in FIG. 4, during installation the second barbed portion 60 and raised end 70 has disposed thereon a tubular body 80. Known tubular bodies are made of materials flexible enough to allow securement of the tubular body 80 around the second barbed portion 60 and the raised end 70, along with providing an air-tight seal between the adaptor body 15 and the inside diameter of a hole drilled into the slab of a basement or foundation of a building. In one particular example, the tubular body 80 is fabricated from low-VOC content Silicone tubing, available from Dow-Corning. As aforementioned, the interior cavity 82 of the tubular body 80 is adapted to receive the raised end 70 and second barbed portion 60 of the adaptor body 15 and may be of any shape required to produce mating engagement therebetween. Furthermore, in some embodiments one or more optional seals (not shown) may be placed around the barbs 61 of the second barbed portion 60 to help effectuate an air-tight seal between the tubular body 80 and the adaptor body 15. It is also known to coat or otherwise cover the interior cavity of the tubular body 80 and/or the exterior of the second barbed portion 60 and/or raised end 70 with a high friction material for facilitating the engagement therebetween. Tubular body lengths may vary, depending upon the length between the collar portion 50 and the distal end 15b of the adaptor body 15. In one example, the length of the tubular body 80 is approximately 3.75 inches. Likewise, the outside diameter of exemplary embodiments of the tubular body 80 may vary depending upon the inside diameter of the hole drilled or bored within the slab of concrete or other foundation of a building or other structure.

Particularly, in a normal assembled installation state as seen in FIG. 4, the tubular body 80 is wedged between the second barbed portion 60 and/or the raised end 70, and the inside wall of the drilled or cored hole that extends through the foundation slab. In some methods of installation, the tubular body 80 is releasably secured around the second barbed portion 60 before the device is installed within the cored hole. In other embodiments, an installation tool 100, as seen in FIGS. 5a and 5b may apply pressure on a portion of the adaptor body 15 to effectuate installation within the cored hole.

During installation and/or extraction the tool 100 may include an inner body 110 that includes a contacting portion 112 at a first end 110a with an aperture 114 that complements the cross-sectional geometry of the engaging portion 30. In one example, the contacting portion 112 may be secured to the inner body 110 by one or more fasteners 116. However, in other examples the contacting portion 112 may be integral with the inner body 110, such as by welding, etc. The tool 100 may facilitate installation by allowing an individual to place the inner body 110 over and/or around the engaging portion 30 wherein at least a portion of the inner face of the contacting portion 112 of the tool 100 may contact the engaging portion 30 and/or at least a portion of the outer face of the contacting portion 112 may contact the collar portion 50 to allow the individual to strike a second portion of the tool 100 with a hammer or other object to facilitate installation of the adaptor body 15.

In other embodiments, an installation tool 100, as seen in FIGS. 5a and 5b may apply pressure on a portion of the adaptor body 15 to effectuate installation within the cored hole. In this embodiment, the contacting portion 112 may be positioned over and around the engaging portion 30, wherein at least a portion of the inner face of the contacting portions 112 of the tool 100 may contact the engaging portion 30 and/or at least a portion of the outer face of the contacting portion 112 may contact the collar portion 50 when the inner body 110 is turned approximately ninety degrees. In some examples, a surface of the contacting portion 112 or inner body 110 may include one or more raised surfaces 118 or other stopping device adapted to prohibit an individual from turning the inner body 110 of the tool 100 beyond a desired location, to effectuate contact with the device for installation and/or removal.

Exemplary embodiments of the inner body 110 are tubular in cross-sectional geometry. In some examples, it may be preferred that the inner body 110 is substantially cylindrical. The inner body 110 may include a threaded surface 117 located towards a second end 110b. The threaded surface 117 may be integral with the inner body 110, or may be a separate piece adhered to within or to the inner body 110. The threaded surface 117 is adapted to complement the threaded surface of a bolt or other threaded fastener 130, described later and seen in FIGS. 5a and 5b.

In some examples, the tool 100 may further include an outer body 120 that is tubular in cross-sectional geometry. In the example depicted in FIGS. 5a and 5b, the outer body 120 is substantially cylindrical in cross-sectional geometry to complement the geometry of the inner body 110. The first end of the outer body 120 contains an aperture 122 large enough to allow the outer body 120 to be positioned around the inner body 110.

Furthermore, some exemplary embodiments of the outer body 120 may include a top portion 124 with an aperture 126 located towards the second end thereof. In the example depicted in FIGS. 5a and 5b, the top portion 124 is a plate adhered to the second end of the outer body 120. However, in other embodiments, the top portion 124 may be optionally secured with the outer body 120 by fasteners or other securing devices.

During one exemplary method of extraction of the adaptor body 15, an individual may releasably secure the inner body 110 with the device as aforementioned. After the inner body 110 is secured with the adaptor body 15, the individual may position the outer body 120 around the inner body 110, as depicted in FIGS. 5a and 5b, wherein at least a portion of the outer body 120 engages the concrete slab 200. The individual places a bolt or other threaded fastener 130 down through the aperture 126 located towards the second end. An optional washer 132 or similar device may be used to help distribute the force exerted on the head of the threaded fastener 130. An individual may then rotationally engage the threaded fastener 130 with the complementary threaded surface 117, effectuating the removal of the device, as seen in FIG. 5b.

Likewise, the complementary portion of the tool 100 may be placed over and around the engaging portion 30, then rotated approximately ninety degrees so that the adaptor body 15 may be removed. In other embodiments, an installation tool 100, as seen in FIGS. 5a and 5b may apply pressure on a portion of the adaptor body 15 to effectuate installation and/or removal within the cored hole.

In some installation methods, the adaptor body is pressed downward in the cored hole until the collar engages the slab. However, some exemplary embodiments of the adaptor body may install wherein the adaptor body is mounted flush to accommodate a larger hole that is drilled deep enough to allow the first barbed portion to lie below the surface of the slab. In this exemplary embodiment, the entire adaptor body is mounted at least flush, if not below the surface level of the slab, decreasing the likelihood that the device may be damaged after installation. Installation of exemplary embodiments of the adaptor body may be installed into a one-inch diameter hole cored through the slab of concrete or other foundation material. The cored hole provides a smoother bonding surface and can be accomplished using a standard, hand-held coring machine. Exemplary embodiments of the adaptor body may be driven into the cored hole using a hammer or similar device.

Installation of exemplary embodiments of the adaptor body may force the flexible silicone tubular body located on at least a portion of the exterior surface thereof against the interior wall of the cored hole, effectuating an air-tight, or almost air-tight, seal between the cored slab and the device. Exemplary embodiments of the adaptor body may then be connected to a portion of the sampling tubing via an air-tight barbed fitting.

As mentioned above, it is also possible to manually install known adaptor body devices and accouterments within the foundation of a home, building or other surface that contains a foundation made of concrete or similar substance. Whether designed for manual or automatic operation, known devices, as well as those of the present innovation, may be generally associated with an automatic soil gas reading device (not shown). Such a soil gas reading device is operative to automatically read the VOC levels of the native material 400 such as soil and/or gravel backfill 300 contained under the foundation wherein such devices are installed, such as depicted in FIGS. 4-5b.

Figure 7:
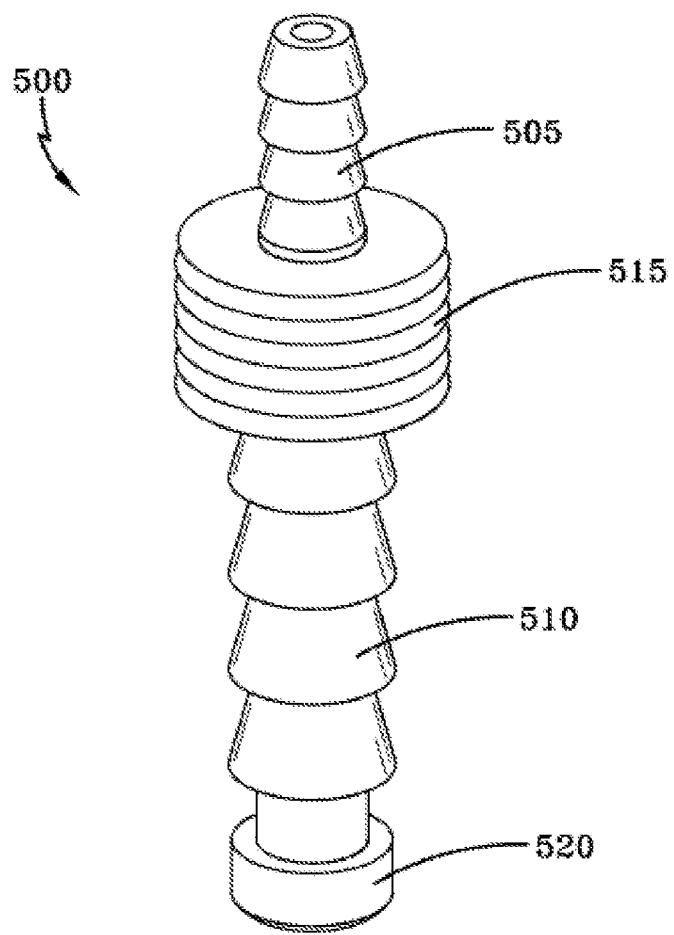
FIG. 7 is a front perspective view of a further exemplary embodiment of an adaptor body in accordance with an aspect of the innovation.

FIG. 7 illustrates another exemplary embodiment of a known adaptor body 500. In this embodiment, the adaptor body 500 has a first barbed end 505 and second barbed end 510. The adaptor body 500 also has a male threaded collar 515 separating the first barbed portion 505 and the second barbed portion 510. A raised end 520 is provided at the distal end of the second barbed portion 510. As discussed herein, the first barbed portion 505 is sized and adapted to facilitate a connection between the adaptor body 500 and a soil gas measuring device (not shown). The second barbed portion 510 is sized and adapted for insertion into a tube 80. The adaptor body 500 may have a unitary design or it may be constructed of modular sections. A modular construction would allow the first 505 and second 510 barbed portions and the threaded collar 515 to be changed to accommodate different sized components, thereby giving the adaptor body 500 greater flexibility. The adaptor body 500 may be made of brass or other material sufficiently strong to withstand the installation and extraction process. To allow soil gas samples to be taken, the adaptor body 500 has an internal passageway through which the soil gas may travel.

Figure 8:
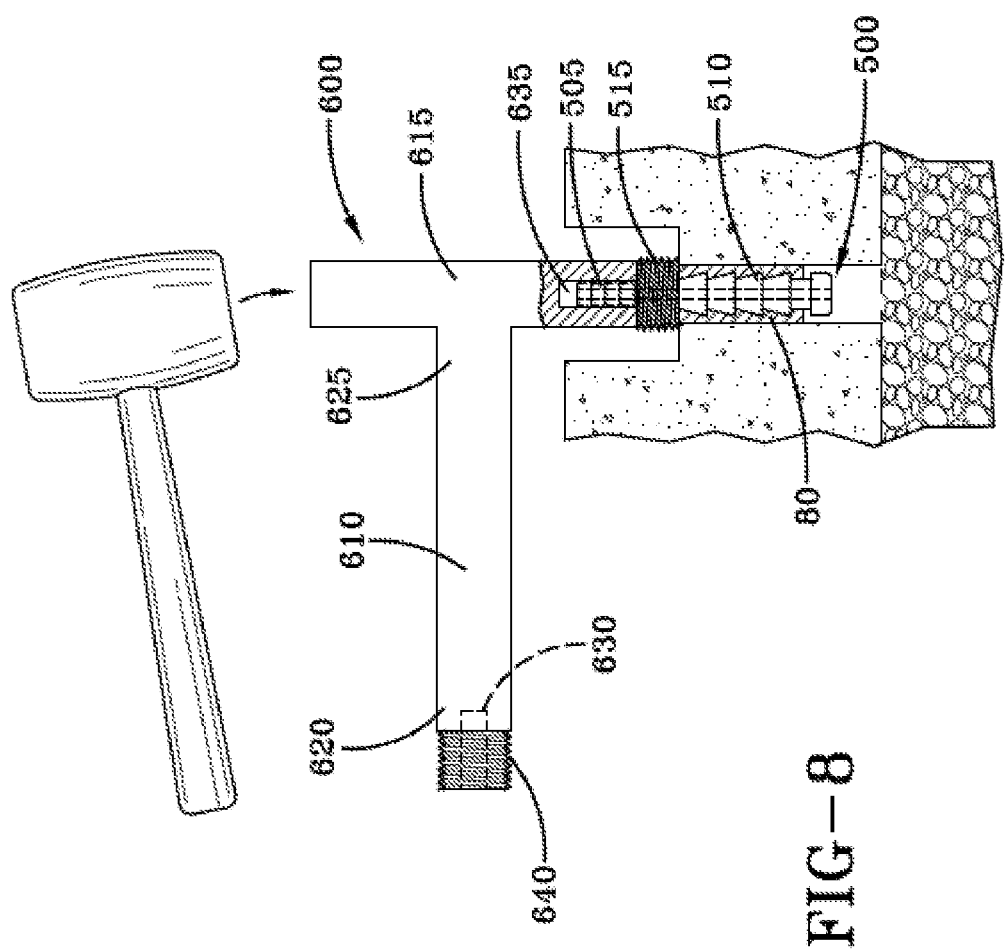
FIG. 8 is a side view of an exemplary tool being used to install the adaptor device and tubular body of FIG. 7 in accordance with an aspect of the innovation.

The adaptor body 500 is also known to be installed and extracted using an exemplary embodiment of a tool 600. FIG. 8 illustrates another exemplary tool 600 used for the installation and extraction of the adaptor body 500. As shown, a known tool 600 has a T-shaped body. The tool 600 includes a stem portion 610 and a handle portion 615. As shown in FIG. 8, the stem 610 has a first end 620 and second end 625. The second end 625 intersects the handle 615 so that the stem portion 610 extends substantially perpendicular from the handle 615. The first end 620 of the stem portion 610 is threaded and has an extraction cavity 630 therein. The threaded portion 640 of the first end 620 is a predetermined length sufficient for extraction of the adaptor body 500, as will be discussed herein. To install the adaptor body 500, the handle has at least one installation cavity 635 therein. As shown in FIG. 8, the installation cavity 635 is adapted to accommodate the first barbed end 505 of the adaptor body 500.

To install the adaptor body 500 using the tool 600, the first barbed end 505 is inserted into the installation cavity 635 in the handle 615. The tool 600 rests on a surface created by the threaded collar 515. A mallet or other device is then used to strike the end of the handle 615 opposite of the installation cavity 635 in order to force the adaptor body 500 into the drilled core (as shown in FIG. 8). After installation of the adaptor body 500, the tool 600 is simply removed from the adaptor body 500 and the adaptor body 500 is connected to a soil gas measuring device.

Figure 10:
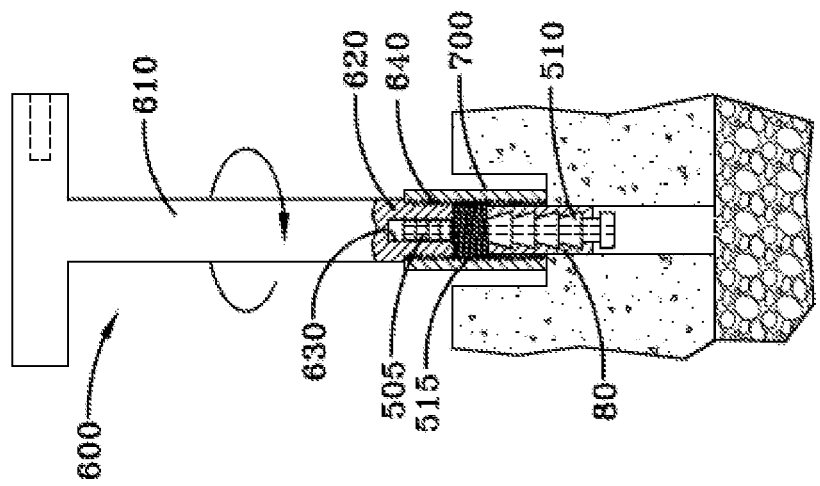
FIG. 10 illustrates a further view of the extraction process thereof in accordance with an aspect of the innovation.
Figure 9:
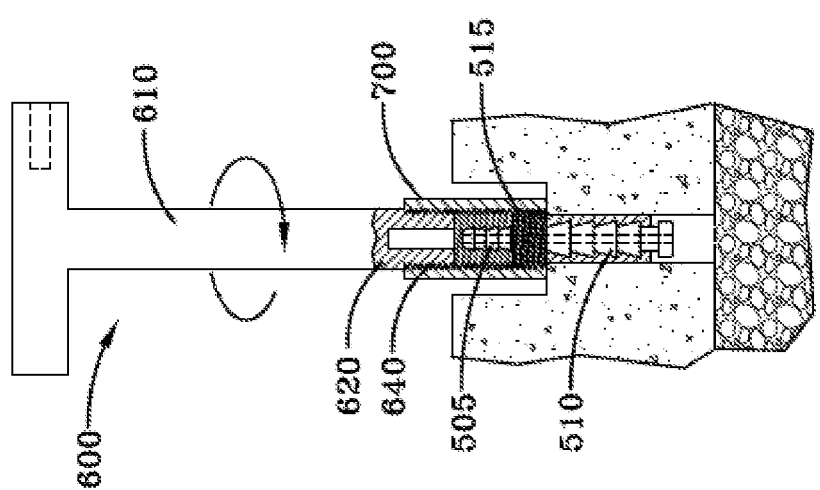
FIG. 9 illustrates the tool of FIG. 8 being used to remove adaptor body and tubular body of FIG. 7 in accordance with an aspect of the innovation.

A typical extraction of the adaptor body 500 is illustrated in FIGS. 9 and 10. The threaded portion 640 of the first end 620 of the stem 610 is threaded into the coupling 700. The coupling 700 is threaded completely onto the pre-determined length of the threaded portion 640. The tool 600 is then used to thread the coupling 700 onto the threaded collar 515 of the adaptor body 500. The coupling 700 can be threaded onto the adaptor body 500 then the tool 600 may be threaded into the coupling 700.

To extract the adaptor body 500 from the core, a user continues to turn the tool 600. Due to the threaded connection between the adaptor body 500 and the coupling 700, the adaptor body 500 is forced upward into the coupling 700. As the adaptor body 500 is raised upward as a result of the rotational motion of the tool 600, the first barbed portion 505 of the adaptor body 500 is inserted into the extraction cavity 630. This enables the adaptor body 500 to be moved upward without the need to readjust the tool 600. Once the threaded collar 515 comes into contact with the first end 620 of the tool 600, the tool 600 can be used to lift the adaptor body 500 from the drilled core.

In still other exemplary embodiments, rather than having a male threaded portion at the first end 620, the first end may have a female threaded portion (not shown in the figures). The female threaded portion may be sufficiently sized to be threaded onto the threaded collar 515 of the adaptor body 500. In this embodiment, the need for a coupling 700 may be avoided.

Figure 11:
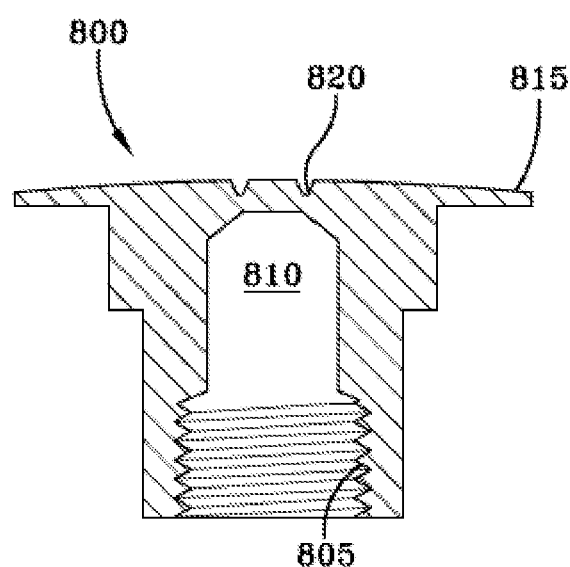
FIG. 11 is a sectional view of an exemplary covering for exemplary embodiments of the adaptor body in accordance with an aspect of the innovation.
Figure 12:
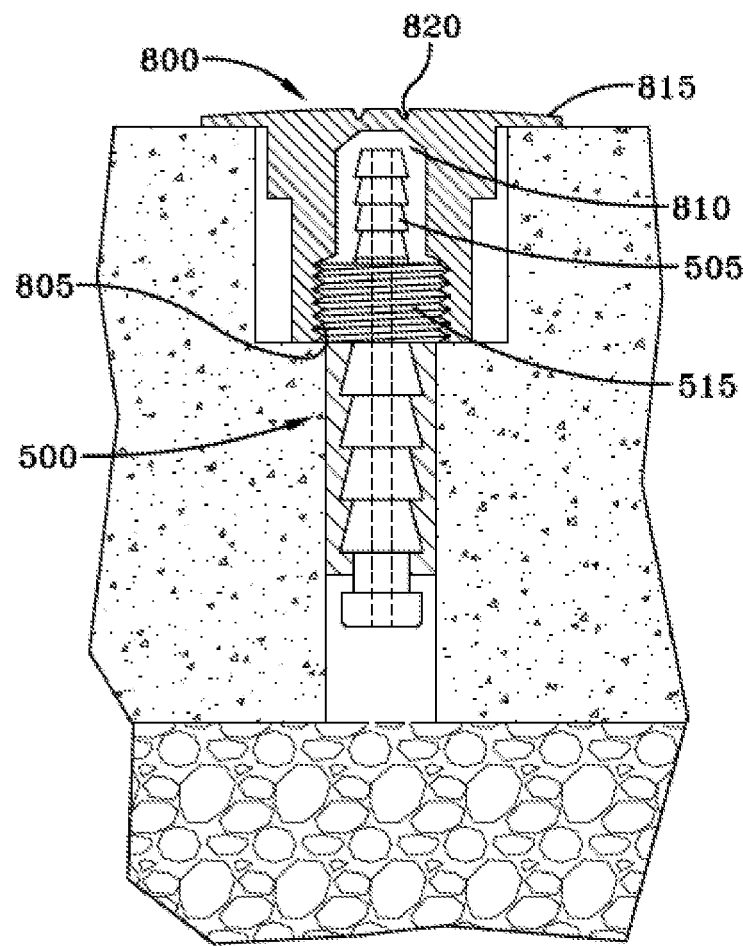
FIG. 12 is a sectional view of an exemplary covering engaged with an exemplary adaptor body installed in a foundation slab in accordance with an aspect of the innovation.

After the adaptor body 500 is installed, a covering 800 may be used to cover the hole created and to protect the adaptor body 500. As illustrated in FIG. 11, the covering 800 includes a threaded portion 805, a cavity 810, a flange 815, and slotted portion 820. FIG. 12 further illustrates the exemplary covering 800 joined with the adaptor body 500. As shown, the covering 800 is lowered onto the adaptor body 500 so that the first barbed portion 505 is recessed within the cavity 810. To secure the covering 800, the threaded portion 805 of the covering 800 is threaded over the threaded portion 515 of the adaptor body 500. The proper covering 800 fit results in the flange 815 of the covering 800 resting atop and being drawn to the surface of the material in which the adaptor body 500 rests. To fully tighten down the covering 800, a screwdriver or other similar device may be used in the slotted portion 820.

To stand up to wear and tear, the covering 800 may be constructed from metal or other materials that are strong enough to protect the adaptor body 500. Before the covering 800 is applied to the adaptor body 500, a cap (not shown in the figures) may be placed over the first barbed portion 505 to prevent debris from entering the adaptor body 500. Although the slotted portion 820 shown is for a spanner screwdriver, it also known to be designed to accommodate flat, Phillips, and hex head screwdrivers as well as other tools.

While the advent of the prior art devices generally described above has largely brought with it vastly improved techniques to the field sub-slab soil gas collection, sampling and analysis, recent advances in the field have developed a surprising increase in demand for soil gas collection and analysis at points beneath the slab. While preferred known techniques are viewed as superior in that they, for example, provide reduced or eliminated leakage, are unobtrusive with respect to the interior of a building when installed, and have dramatically reduced the cost and difficulties of installation over previously-used devices, they have been found impractical to use in connection with other, external sampling devices placed within the sampling hole or used to collect samples at points beneath the slab.

There is also a desire in the field for the ability to collect for analysis samples of sub-slab soil gas at a source that lies beneath the slab itself, or coincident with or adjacent to the base of the slab. Known prior art devices provide no extensibility, and therefore must be manufactured at a length appropriate to reach the desired point of collection or a large-diameter hole must be cored to a further depth in order to seat known devices lower in relation to the top surface of the slab. It has also been discovered that sub-slab soil gas collection at points at or beneath the bottom surface of the slab is often impractical with known devices due to contamination, blockage and clogging, and moisture collection concerns.

The invented system also provides certain improvements in the collection, sampling and analysis process of sub-slab soil gas in view of repeated sampling that often occurs at multiple locations. For instance, foundation slab thicknesses may often vary from location to location to such an extent that those in the field must either obtain multiple sizes of the prior art devices described above, or obtain often unobtainable knowledge of slab thickness prior to coring, in order to align the ingress opening of the device at a precise position relative to the top or bottom surface of the slab involved.

To overcome these and other drawbacks with the current art, the present innovation utilizes in part an improved adaptor body relative to known devices. As will be explained in further detail below, exemplary embodiments of the new adaptor body have a length and proximal and distal ends, and are generally provided with a first barbed portion disposed at the proximal end of the adaptor body, a second barbed portion disposed at the distal end of the adaptor body, a collar portion disposed between the first barbed portion and the second barbed portion, and an internal cavity having an interior surface and passing through the length of the adaptor body. The aforementioned features are similar in function and variety to those described above in exemplary prior art adaptor bodies, for example adaptor bodies 15 and 500 shown in FIGS. 1 and 7, respectively. Exemplary adaptor bodies used in the invented system, however, also include at least a coupling portion having an internal thread disposed on the interior surface and extending longitudinally thereon from the distal end of the adaptor body. In this way, the internal cavity through which soil gas is collected and drawn from the proximal end of the adaptor body for analysis may be extended via other extension components of the invented system, as further described herein.

Figures 13A, 13B, 13C:
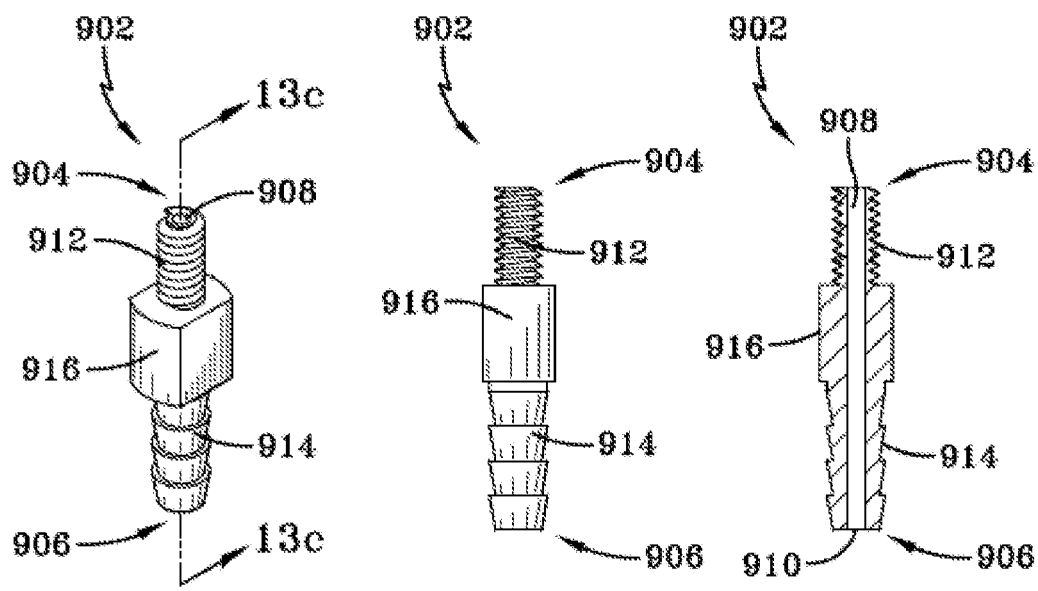
FIG. 13a is a perspective view of an exemplary embodiment of a fitting extension component of the invented sampling system in accordance with an aspect of the innovation.
FIG. 13b is a front elevation view thereof in accordance with an aspect of the innovation.
FIG. 13c is a sectional view thereof in accordance with an aspect of the innovation.

One exemplary component of the invented system may be, for instance, a fitting extension 902 as illustrated in FIGS. 13*a*, 13*b* and 13*c*. FIG. 13*a* shows a perspective view of an exemplary embodiment of a fitting extension 902, FIG. 13*b* shows a front elevation view of the fitting extension 902, and FIG. 13*c* shows a sectional view of the fitting extension 902 (taken through line 13*c*-136*c* shown in FIG. 13*a*) from the perspective of FIG. 13*b*. Referring to these figures, the fitting extension 902 is shown having first 904 and second 906 ends generally defining a length therebetween. An internal cavity 908 extends longitudinally through the extension 902 from the first end 904 to an outlet 910 at the second end 906. In preferred embodiments, the diameter of the cavity 908 is commensurate with or equal to the diameter of the internal cavity of the adaptor body (e.g., see FIGS. 17-18).

The exemplary fitting extension 902 is shown having an attachment means that is complimentary with an improved embodiment of the adaptor body as further detailed herein below. The fitting extension 902 preferably utilizes an external thread 912 disposed at the first end 904, which is adapted for complimentary threaded retention within a coupling portion of the adaptor body. The fitting extension 902 may also include a fitting portion 914 disposed at the outlet 910 at the second end 906 of the extension 902. Generally, the fitting portion 914 may be embodied in a number of structures complimentary with other sampling devices or components. In a preferred embodiment of the fitting extension 902 as shown in FIG. 13*a*, the fitting portion is a barb portion 914 disposed at the outlet 910. The barbed portion 914 generally includes at least one conical-frustum shaped barb, for example, and facilitates the releasable securement of tubing to connect the system to other sampling devices or to extend the effective length of the internal cavity and thus the sampling depth.

The fitting extension 902 may further include an external engaging portion 916. The external engaging portion 916 generally provides a geometry suitable for engagement with a hand tool such as a wrench or other tool that is useful for assembling and disassembling the components of the invented sampling system. In one embodiment, the external engaging portion 916 is disposed between the external thread 912 and the barbed portion 914. The external engaging portion 916 depicted here is of substantially circular shape with a pair of opposed sides that are substantially parallel to one another. The opposing sides may be described as secants of the substantially circular shape. In other embodiments, the external engaging portion may be substantially hexagonal or square in cross-sectional shape, or other such geometries suitable for use with a wrench or other tools to provide a mechanical advantage.

Figures 14A, 14B, 14C:
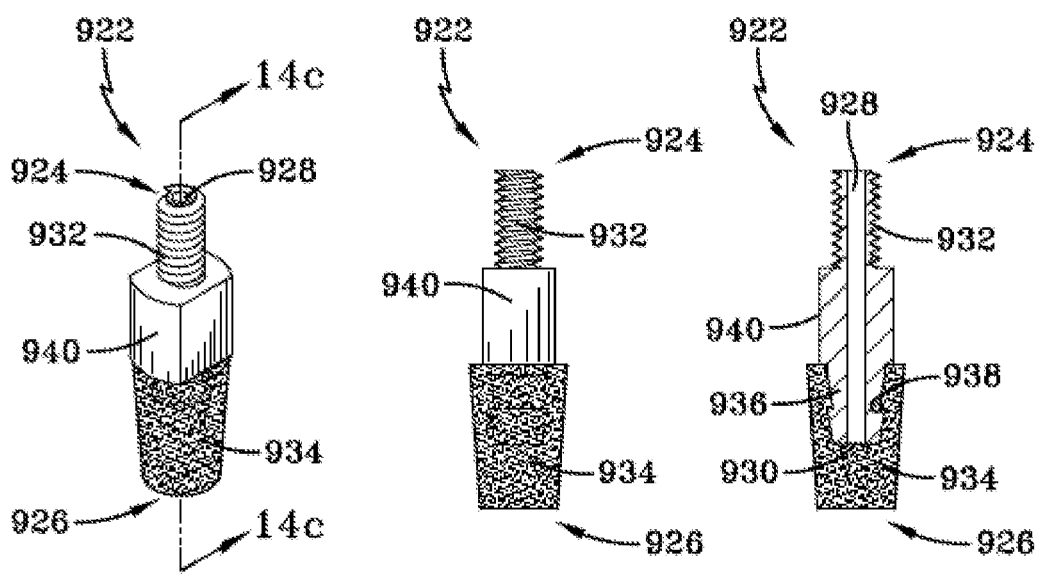
FIG. 14a is a perspective view of an exemplary embodiment of a filter extension component of the invented sampling system in accordance with an aspect of the innovation.
FIG. 14b is a front elevation view thereof in accordance with an aspect of the innovation.
FIG. 14c is a sectional view thereof in accordance with an aspect of the innovation.

Another exemplary component of the invented system may be, for instance, a filter extension 922 as illustrated in FIGS. 14*a*, 14*b* and 14*c*. FIG. 14*a* shows a perspective view of an exemplary embodiment of a filter extension 922, FIG. 14*b* shows a front elevation view of the filter extension 922, and FIG. 14*c* shows a sectional view of the filter extension 922 (taken through line 14*c*-14*c* shown in FIG. 14*a*) from the perspective of FIG. 14*b*. Referring to these figures, the filter extension 922 is shown having first 924 and second 926 ends generally defining a length therebetween. An internal cavity 928 extends longitudinally through the extension 922 from the first end 924 to an outlet 930 at the second end 926. In preferred embodiments, the diameter of the cavity 928 is commensurate with or equal to the diameter of the internal cavity of the adaptor body (e.g., see FIGS. 17-18).

The exemplary filter extension 922 is shown having an attachment means that is complimentary with an improved embodiment of the adaptor body as further detailed herein below. The filter extension 922 preferably utilizes an external thread 932 disposed at the first end 924, which is adapted for complimentary threaded retention within a coupling portion of the adaptor body. The filter extension 922 may also include a filter element 934 disposed at the outlet 930 at the second end 926 of the extension 922. In some embodiments, the filter extension 922 includes a barbed portion 936 with the filter element 934 attached thereto. The barbed portion 936 generally includes at least one conical-frustum shaped barb for retainment within an attachment aperture by complimentary engagement between one or more internal ribs 938 of the filter element 934. In one embodiment, the filter element 934 is made of a sintered porous metal.

The filter extension 922 may further include an external engaging portion 940. The external engaging portion 940 generally provides a geometry suitable for engagement with a hand tool such as a wrench or other tool that is useful for assembling and disassembling the components of the invented sampling system. In one embodiment, the external engaging portion 940 is disposed between the external thread 932 and the barbed portion 936 or filter element 934. The external engaging portion 940 depicted here is of substantially circular shape with a pair of opposed sides that are substantially parallel to one another. The opposing sides may be described as secants of the substantially circular shape. In other embodiments, the external engaging portion may be substantially hexagonal or square in cross-sectional shape, or other such geometries suitable for use with a wrench or other tools to provide a mechanical advantage.

Figures 15A, 15B, 15C:
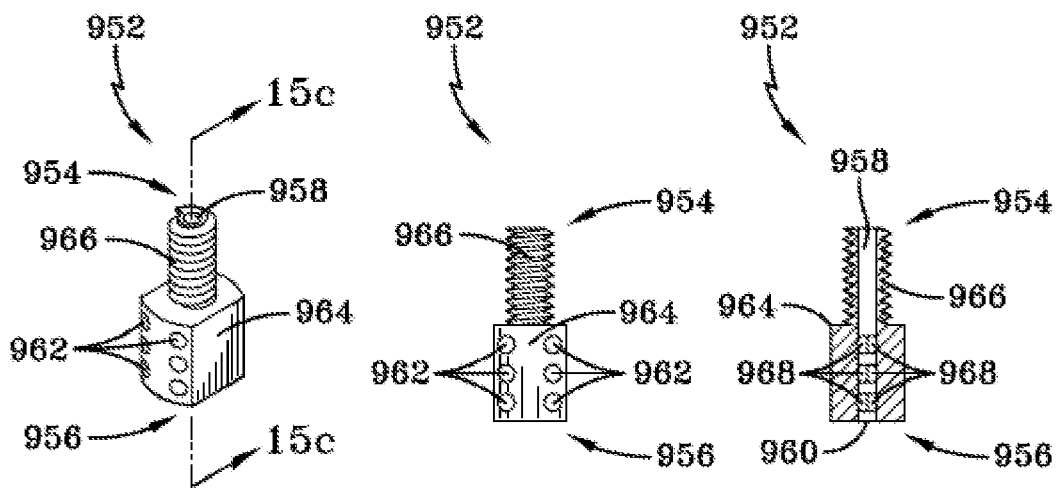
FIG. 15a is a perspective view of an exemplary embodiment of a sieve extension component of the invented sampling system in accordance with an aspect of the innovation.
FIG. 15b is a front elevation view thereof in accordance with an aspect of the innovation.
FIG. 15c is a sectional view thereof in accordance with an aspect of the innovation.

Another exemplary component of the invented system may be, for instance, a sieve extension 952 as illustrated in FIGS. 15a, 15b and 15c. FIG. 15a shows a perspective view of an exemplary embodiment of a sieve extension 952, FIG. 15b shows a front elevation view of the sieve extension 952, and FIG. 15c shows a sectional view of the sieve extension 952 (taken through line 15c-15c shown in FIG. 15a) from the perspective of FIG. 15b. Referring to these figures, the sieve extension 952 is shown having first 954 and second 956 ends generally defining a length therebetween. An internal cavity 958 extends longitudinally through the extension 952 from the first end 954 to an outlet 960 at the second end 956. In preferred embodiments, the diameter of the cavity 958 is commensurate with or equal to the diameter of the internal cavity of the adaptor body (e.g., see FIGS. 17-18).

The sieve extension 952 may include a plurality of lateral outlets 962 each intersecting with the internal cavity 958 to provide alternate pathways through which sub-slab soil gas may enter the system. The lateral outlets 962 are depicted in FIGS. 15a-15c in addition to the primary outlet 960; however those skilled in the art will appreciate that the primary outlet 960 may be left open or closed in various embodiments of the innovation. In preferred embodiments, six lateral bores, or outlet cavities 968, intersecting with the internal cavity 958 are provided for a total of twelve lateral outlets 962, although more or less may be provided without departing from the invented system. For example, while the preferred embodiment shown is provided with three pair of outlet cavities 968 extending laterally through the sieve extension 952—in an intersecting "X" pattern—any practical number and configuration that provides alternate pathways for sub-slab soil gas collection is considered known and encompassed by the instant innovation.

In some embodiments, the plurality of lateral outlets 962 is located on an external engaging portion 964 of the sieve extension 952. The external engaging portion 964 depicted here is of substantially circular shape with a pair of opposed sides that are substantially parallel to one another. The opposing sides may be described as secants of the substantially circular shape. In other embodiments, the external engaging portion may be substantially hexagonal or square in cross-sectional shape, or other such geometries suitable for use with a wrench or other tools to provide a mechanical advantage.

The exemplary sieve extension 952 is shown having an attachment means that is complimentary with an improved embodiment of the adaptor body as further detailed herein below. The fitting extension 952 preferably utilizes an external thread 966 disposed at the first end 954, which is adapted for complimentary threaded retention within a coupling portion of the adaptor body.

Figures 16A, 16B, 16C:
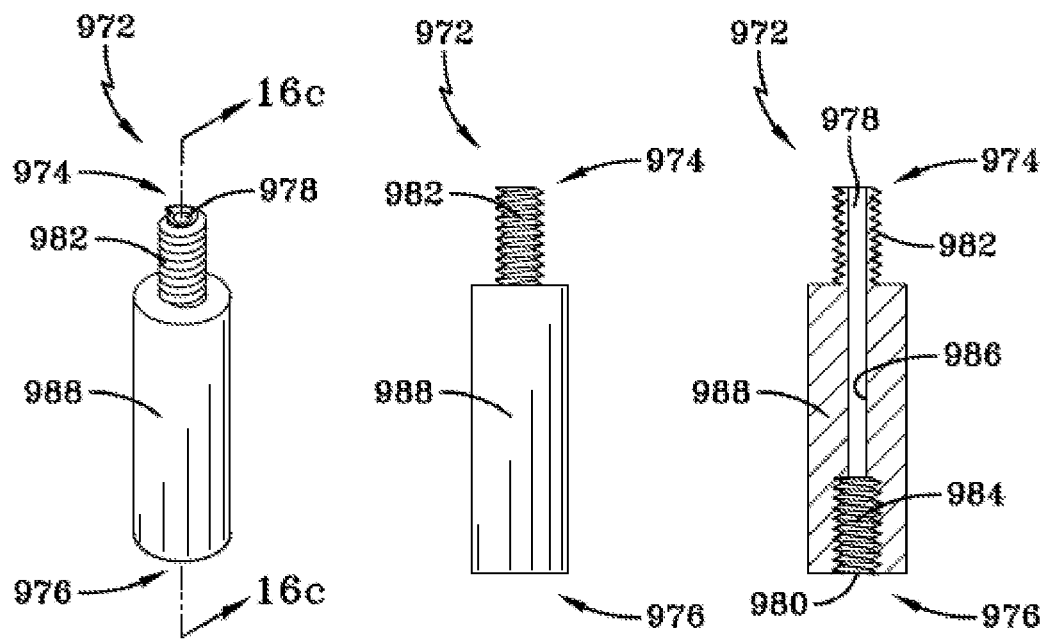
FIG. 16a is a perspective view of an exemplary embodiment of a length extension component of the invented sampling system in accordance with an aspect of the innovation.
FIG. 16b is a front elevation view thereof in accordance with an aspect of the innovation.
FIG. 16c is a sectional view thereof in accordance with an aspect of the innovation.

Another exemplary component of the invented system may be, for instance, a length extension 972 as illustrated in FIGS. 16a, 16b and 16c. FIG. 16a shows a perspective view of an exemplary embodiment of a length extension 972, FIG. 16b shows a front elevation view of the length extension 972, and FIG. 16c shows a sectional view of the length extension 972 (taken through line 16c-16c shown in FIG. 16a) from the perspective of FIG. 16b. Referring to these figures, the length extension 972 is shown having first 974 and second 976 ends generally defining a length therebetween. An internal cavity 978 extends longitudinally through the extension 972 from the first end 974 to an outlet 980 at the second end 976. In preferred embodiments, the diameter of the cavity 978 is commensurate with or equal to the diameter of the internal cavity of the adaptor body (e.g., see FIGS. 17-18). The exemplary length extension 972 is also shown having an attachment means that is complimentary with an improved embodiment of the adaptor body as further detailed herein below. The length extension 972 preferably utilizes an external thread 982 disposed at the first end 974, which is adapted for complimentary threaded retention within a coupling portion of the adaptor body.

While a length extension 972 component may simply be utilized to extend the effective sampling depth of the invented system, in preferred embodiments, the length extension 972 is coupled to and between an improved adaptor body and an extension—e.g., the fitting extension 902, the filter extension 922 or the sieve extension 952. In those embodiments, the length extension 972 is further provided with a coupling portion 984 disposed at the second end, wherein the length extension 972 is releasably securable to one of the aforementioned extensions, for instance. In preferred embodiments, the coupling portion 984 is provided as an internal thread disposed on the interior surface 986 of the internal cavity 978. The internal thread extends longitudinally on the interior surface 986 from the second end of the length extension, and is adapted to threadably retain the external thread of a second extension (e.g., 912, 932 or 966).

Some embodiments of the length extension 972 may further include an external engaging portion 988. The external engaging portion generally provides a geometry suitable for engagement with a hand tool such as a wrench or other tool that is useful for assembling and disassembling the components of the invented sampling system, or may simply be provided as a circular surface for hand gripping, as shown in FIGS. 16a-16c. The external engaging portion may also be, for example, substantially circular in shape with a pair of opposed sides that are substantially parallel to one another, as described in connection with other extension embodiments if desired. The opposing sides may be described as secants of the substantially circular shape. In other embodiments, the external engaging portion may be substantially hexagonal or square in cross-sectional shape, or other such geometries suitable for use with a wrench or other tools to provide a mechanical advantage.

Figure 17:
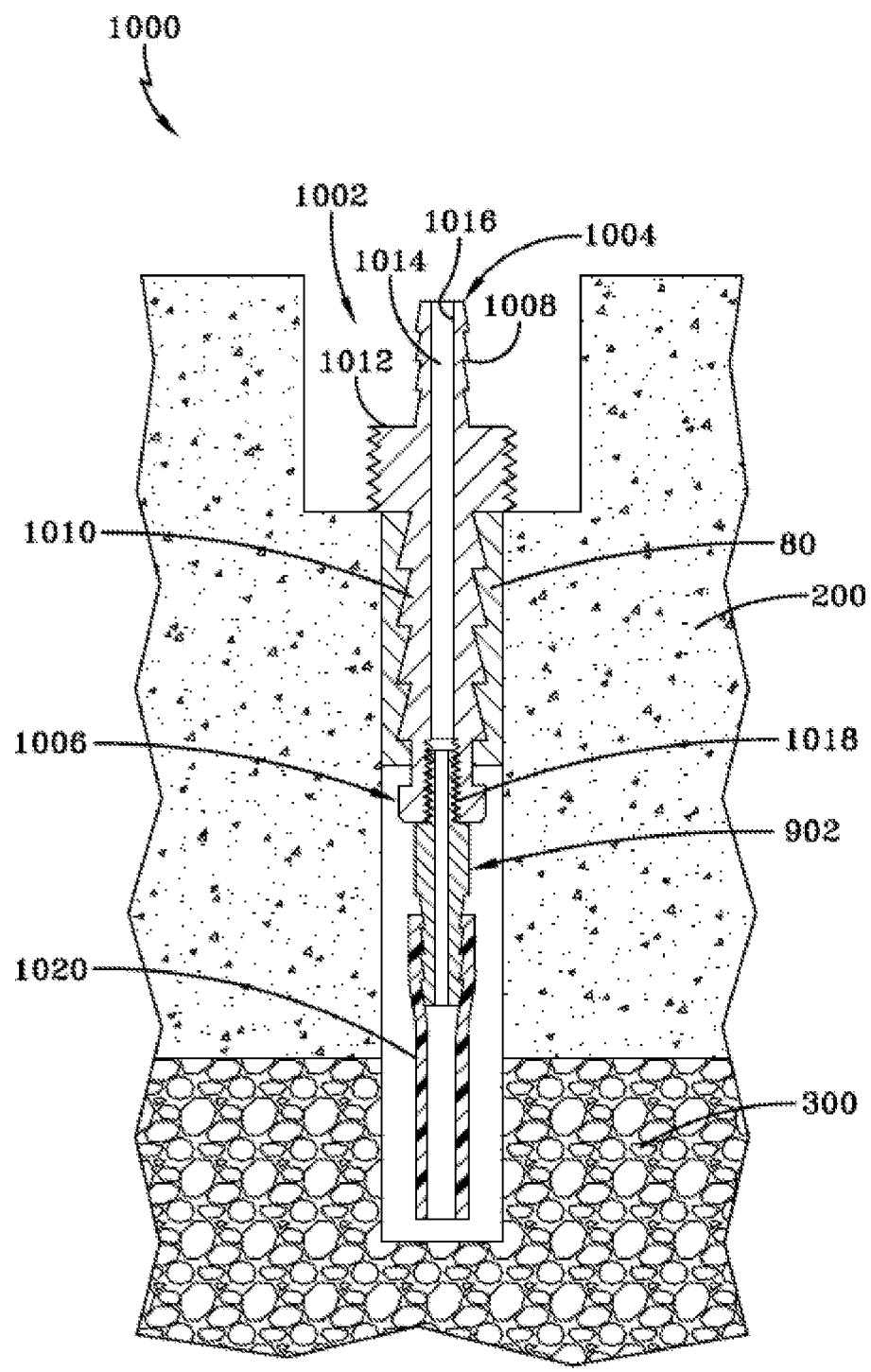
FIG. 17 illustrates a sectional view of an exemplary embodiment of the invented sampling system in use in connection with an exemplary slab in accordance with an aspect of the innovation.

Turning to FIG. 17, a sectional view of an exemplary embodiment of the invented sampling system 1000 in use in connection with an exemplary slab 200 and native material or backfill 300 in illustrated. The invented system 1000 includes an improved adaptor body 1002 having a length and proximal 1004 and distal 1006 ends. The adaptor body 1002 generally includes a first barbed portion 1008 disposed at the proximal end 1004 and a second barbed portion 1010 disposed at the distal end 1006. A collar portion 1012 is disposed between the first 1008 and second 1010 barbed portions, and an internal cavity 1014 having an interior surface 1016 passes through the length of the adaptor body 1002. These basic elements and their variations and equivalents are generally known in the art.

The improved adaptor body 1002, however, further includes a coupling portion 1018 disposed at the distal end 1006 of the adaptor body 1002. In preferred embodiments, the coupling portion 1018 is provided as an internal thread disposed on the interior surface of the internal cavity 1014, extending longitudinally thereon from the distal end 1006 of the adaptor body 1002. The coupling portion 1018 is adapted for complimentary threaded retention of an external thread of an extension, for instance a fitting extension 902 as shown in FIG. 17 and described in more detail in connection with FIGS. 13a-13c. In this exemplary embodiment, a length of tubing, for instance, can be attached to the fitting portion of the fitting extension 902 to provide for additional depth for sampling points.

Figure 18:
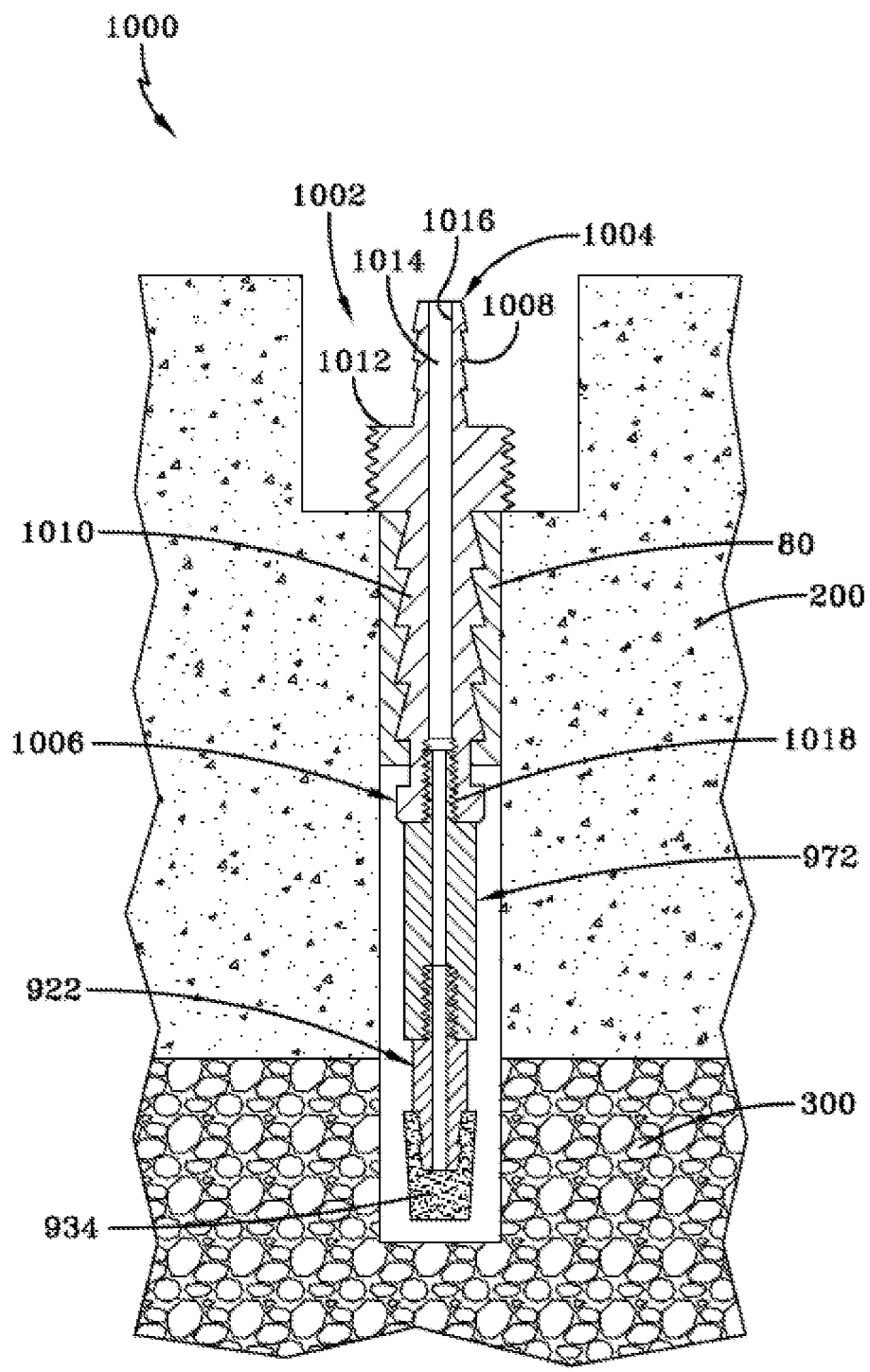
FIG. 18 illustrates a sectional view of a further exemplary embodiment of the invented sampling system in use in connection with an exemplary slab in accordance with an aspect of the innovation.

A sectional view of a further exemplary embodiment of the invented sampling system 1000 in use in connection with an exemplary slab 200 is illustrated in FIG. 18. An exemplary improved adaptor body 1002 is shown as described in further detail in connection with FIG. 17 above. In this embodiment, a length extension 972 is threadably attached to and between the coupling portion 1018 of the adaptor body 1002 and a filter extension 922. This exemplary configuration, for example, permits the user to extend the effective length of the internal cavity 1014 to a sampling point below the slab 200, and further provides a means for filtering particulates from the vapor stream being sampled via the filter element 934.

Figure 19:
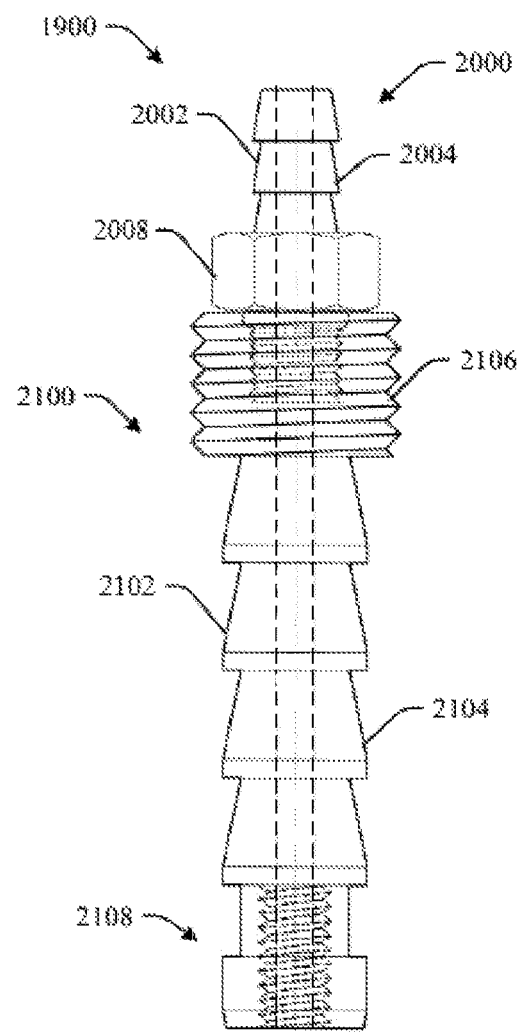
FIG. 19 is another example embodiment of a multi-piece adaptor body in accordance with an aspect of the innovation.
Figure 20:
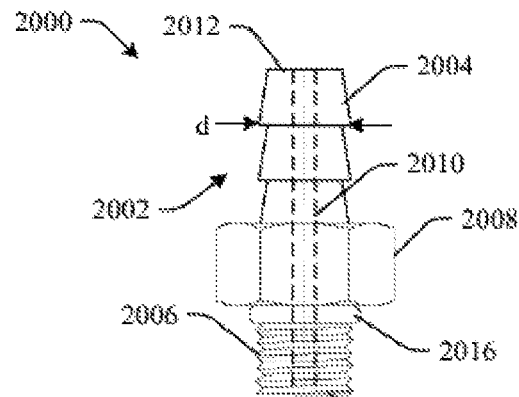
FIGS. 20 and 21 are illustrations of a first portion and a second portion of the multi-piece adaptor body respectively in accordance with an aspect of the innovation.
Figure 21:
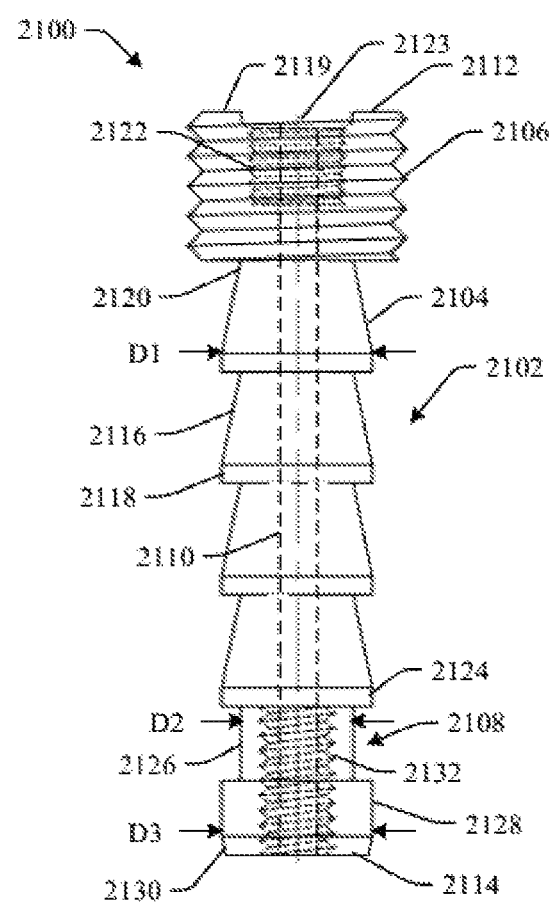

FIGS. 19-21 illustrates another exemplary embodiment of a multi-piece adaptor body 1900 in accordance with an aspect of the innovation. The adaptor body 1900 includes a first body portion 2000 and a second body portion 2100. The first body portion 2000 is removably attached to the second body portion 2100, which facilitates flexibility in use of the adapter body 1900. More specifically, after installation, the first body portion 2000 can be removed to allow a third party (e.g., Swagelok) adapter or fitting to be attached to the second body portion 2100. This allows the user to use different sized tubing (not shown), which connects to the first body portion 2000 or to the third party adapter and thus, connects the adaptor body 1900 with the soil gas measuring device.

The first body portion 2000 is an integrated piece that includes a first barbed end 2002 having at least one barb 2004, a male connector mechanism 2006, a grip portion 2008, and an internal cavity 2010 that axially extends from a first end 2012 to a second end 2014 of the first body portion 2000. The barb 2004 has a conical shape that has a diameter d at its widest part such that the first barbed end 2002 is sized and adapted to facilitate a connection to tubing of the soil gas measuring device.

As will be described further below, the male connector mechanism 2006 is adapted to connect the first body portion 2000 to the second body portion 2100. In the example embodiment described and illustrated in FIG. 20, the male connector mechanism 2006 comprises a male threaded connector 2006 that is adapted to threadedly attach to the second portion 2100. It is to be understood, however, that the first body portion 2000 and the second body portion 2100 may be connected (and disconnected) by other means, such as but not limited to, a quick disconnect coupling, magnetic coupling, etc. Thus, the male connector mechanism 2006 can comprise any type of connection mechanism associated with any type of coupling, such as but not limited to those mentioned above. An O-ring 2018 is provided around the male connector mechanism 2006 to provide a seal between the first body portion 2000 and the second body portion 2100 during the sampling process.

The grip portion 2008 is adapted to allow the user to attach a removal device to the first body portion 2000 to attach and remove the first body portion 2000 from the second body portion 2100. In the example embodiment illustrated in the figures, the grip portion 2008 has a circular shape with multiple flat surfaces similar to that of a bolt to allow the attachment of a removal device (e.g., socket, wrench, etc.). The grip portion 2008, however, can be any suitable grip that facilitates removal of the first portion that coincides with other types of connection means, as disclosed above.

The second body portion 2100 is an integrated piece that includes a second barbed end 2102 having at least one barb 2104, a male threaded collar 2106, a projection portion 2108, and an internal cavity 2110 that axially extends from a first end 2112 to a second end 2114 of the second portion 2100. When the first body portion 2000 and the second body portion 2100 are connected, the internal cavity 2010 of the first body portion 2000 and the internal cavity 2110 of the second portion are aligned such that the internal cavity extends the length of the adaptor body 1900 to allow the gas sample to pass through the adaptor body 1900.

The barb 2104 has a conically shaped part 2116 that has a diameter D1 at its widest part and a cylindrically shaped part 2118 that extends from the widest part of the conically shaped part 2116. This configuration facilitates insertion of the second barbed end 2102 into the tube 80 described above (see FIG. 3a). Further, the presence of the cylindrically shaped part 2118 increases the surface area of the barb 2104 that contacts an inner surface of the tube 80. The increased surface area of the barb 2104 in contact with the inner surface of the tube enhances the stability of the adaptor body 1900 after it is installed.

The male threaded collar 2106 includes a first surface 2119 and is disposed at a first end 2120 of the second barbed end 2102 and is used to install and extract the adaptor body 1900 as described herein. The male threaded collar 2106 includes a first female receiving connector 2122 defined therein. The first female receiving connector 2122 receives the male connector mechanism 2006 to thereby connect the first body portion 2000 to the second body portion 2100 for installation and/or gas sampling. In the example embodiment described and illustrated in FIG. 21, the first female receiving connector 2122 comprises a first female threaded connector 2122 that is adapted to threadedly receive the male threaded connector 2006. As mentioned above, it is to be understood, however, that the first body portion 2000 and the second body portion 2100 may be connected by other means, such as but not limited to, a quick disconnect coupling, magnetic coupling, etc. Thus, the first female receiving connector/mechanism 2122 can comprise any type of receiving connector/mechanism associated with any type of coupling, such as but not limited to those mentioned above. The male threaded collar 2106 is also used to install and extract the adaptor body 1900, as described above. A recess 2123 is defined in the male threaded collar 2106 at an entrance to the first female receiving connector 2122. The recess 2123 receives the O-ring 2016 to prevent gas leakage between the first body portion 2000 and the second body portion 2100 during the sampling process.

The projection portion 2108 is disposed at a second end 2124 of the second barbed end 2102 and includes a first cylindrically projection 2126 having a diameter D2 that is less than D1 and a second cylindrically shaped projection 2128 having a diameter D3 that is substantially the same as Dl. The second cylindrically shaped projection 2128 includes a beveled edge 2130 that facilitates installation of the adaptor body 1900, as described herein. A second female receiving (threaded) connector/mechanism 2132 is defined in the projection portion 2108 that facilitates the addition of extensions, as described above and illustrated in FIGS. 13-18.

Figure 23:
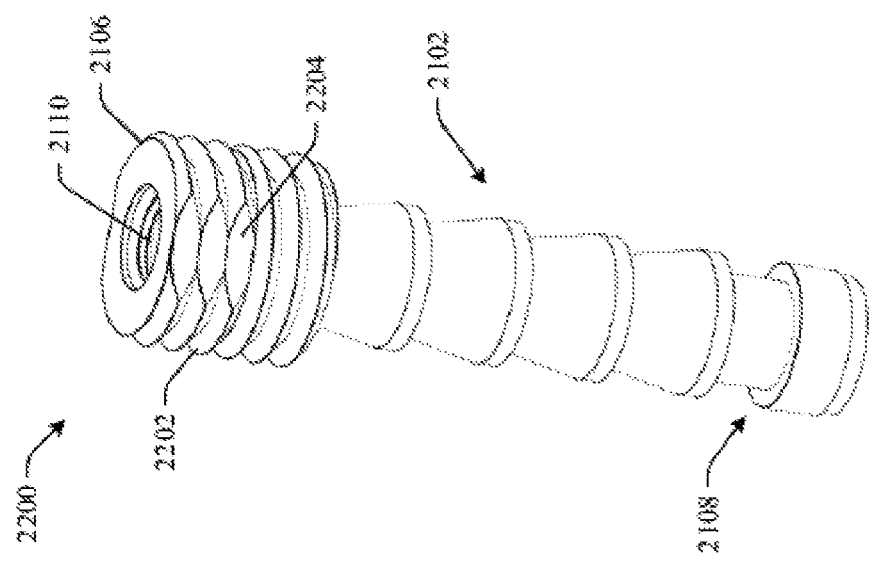
FIGS. 22 and 23 illustrates another embodiment of a multi-piece adaptor body in accordance with an aspect of the innovation.
Figure 22:
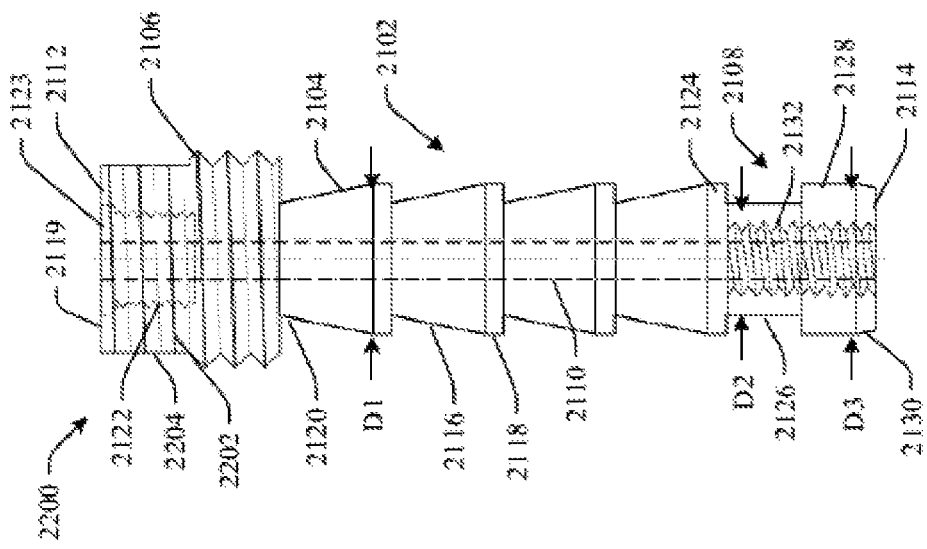

FIGS. 22 and 23 illustrate a perspective and plan view respectively of another embodiment of an adaptor body 2200 in accordance with an aspect of the innovation. The adaptor body 2200 is similar to the adaptor body 1900 illustrated in FIGS. 19-21, thus, similar features between the two example embodiments will not be repeated in the description of the example embodiment illustrated in FIGS. 22 and 23.

The example adaptor body 2200 further includes a means for the user of the adaptor body 2200 to grip the male threaded collar 2106 of the second body portion 2100 to prevent rotation of the second body portion 2100 during removal or attachment of the first body portion 2000 or the third party adaptor from the second body portion 2100. Specifically, at least one thread 2202 of the male threaded collar 2106 may include a flat surface 2204 disposed on opposite sides of the male threaded collar 2106. This configuration allows the user to engage the oppositely disposed flat surfaces on the male threaded collar 2106 and grip the male threaded collar 2106 with a tool (e.g., wrench) to prevent the second body portion 2100 from rotating as mentioned above. It is to be understood that the innovation is not dependent on the number of threads 2202 having oppositely disposed flat surfaces 2204. The number of threads 2202 having flat surfaces 2204 may range from one thread 2202 to all threads. Further, the innovation is not dependent on the number of oppositely disposed flat surfaces 2204.

Figure 24:
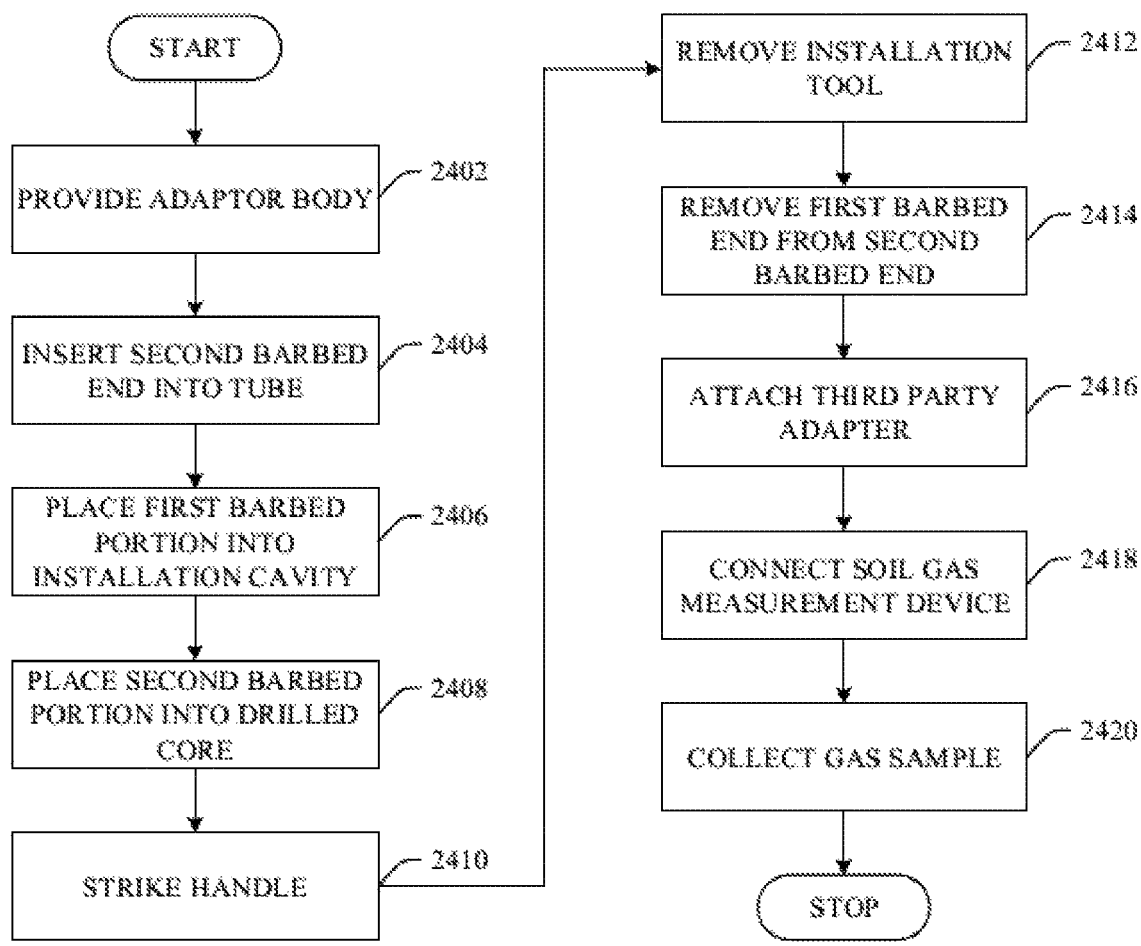
FIG. 24 is a flow chart illustrating a method of collecting gas samples in accordance with an aspect of the innovation.

Referring to FIG. 24, a method of collecting gas samples is described. At 2402, an adaptor body is provided having a first barbed end and a second barbed end. At 2404, inserting at least a portion of the second barbed end into a tubular body. At 2406, placing at least a portion of the first barbed end into the installation cavity in the handle of the installation tool. At 2408, placing the second barbed end into a drilled core. At 2410, striking the handle on an opposite end of the installation cavity to force the adapter body into the drilled core. At 2412, removing the installation handle from the first barbed end. At 2414, removing the first barbed end of the adaptor body from the second barbed end. At 2416, attaching a third party adapter of fitting to the second barbed end. At 2418, connecting a soil gas measurement device to the third party adapter. At 2420, collecting the gas sample.

Figure 25:
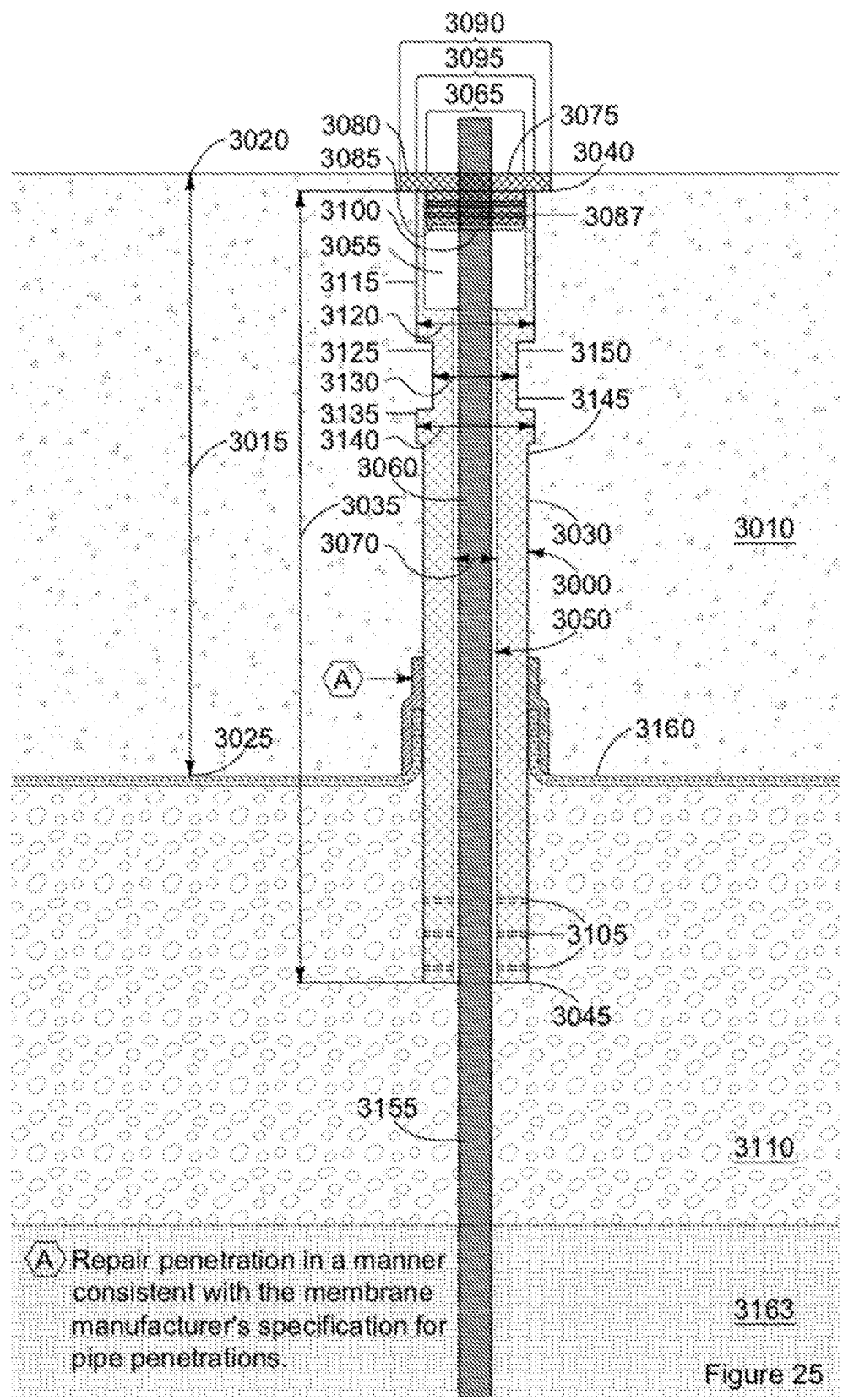
FIG. 25 is an illustration of an installation device in cross-section in accordance with an aspect of the innovation.
Figure 26:
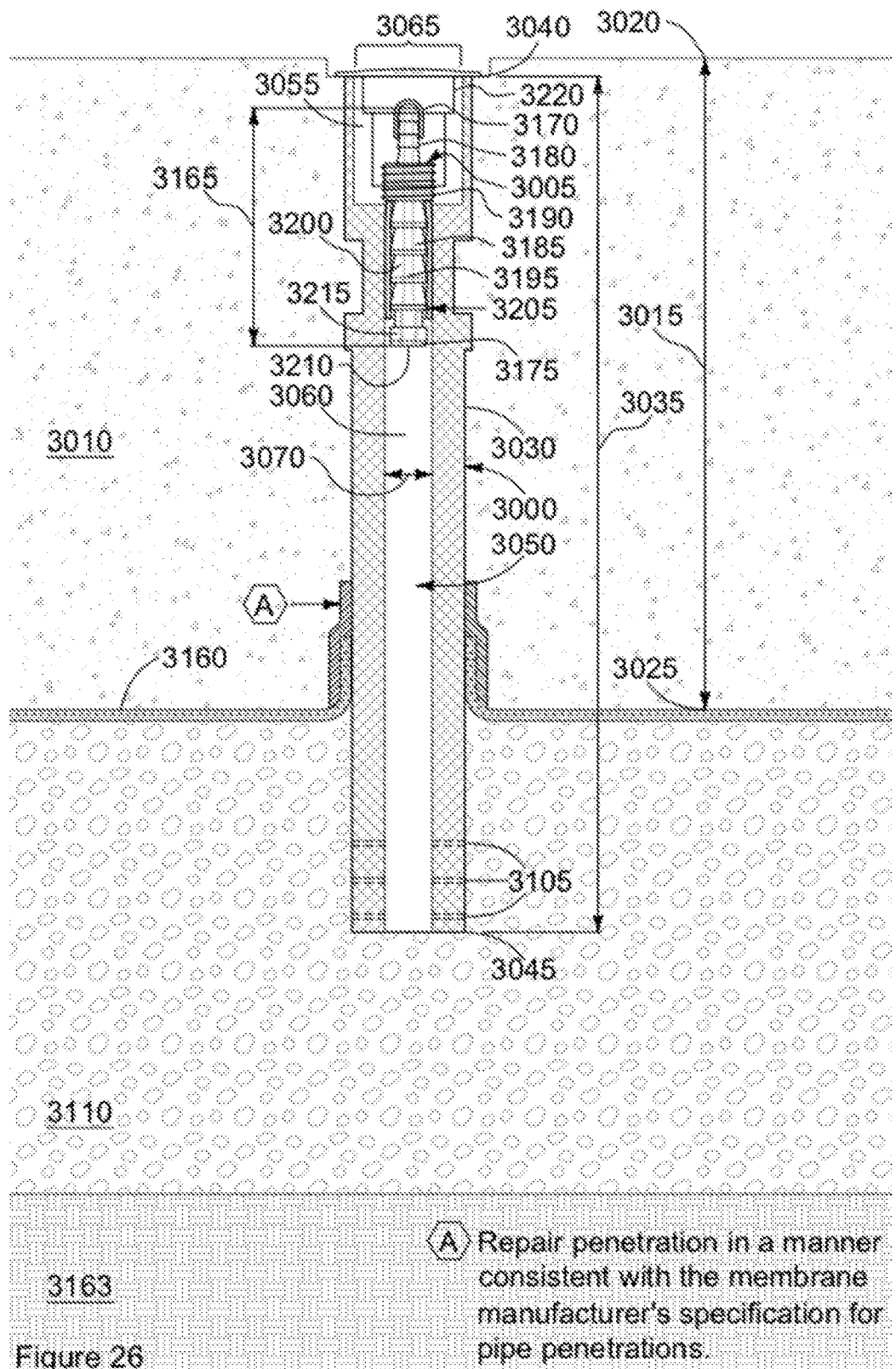
FIG. 26 is an illustration of the installation device in cross-section with an adaptor body received therein in accordance with an aspect of the innovation.

FIGS. 25 and 26 illustrate an installation device 3000 configured to receive another exemplary embodiment of an adaptor body 3005 for facilitating the analysis of samples of sub-slab soil gas in accordance with an aspect of the innovation. The installation device 3000 can be used for installing the adaptor body 3005 in a newly-placed concrete slab or a pre-existing slab. The installation device 3000 can optimize uniformity in use and installation of the adaptor body 3005. The installation device 3000 and adaptor body 3005 can be used to facilitate the collection of soil gas samples and pressure measurements beneath engineered vapor intrusion barriers or vapor mitigation coatings.

FIG. 25 illustrates an installation device 3000 for receiving and installing the adaptor body 3005 for sampling soil gas under a slab 3010. The slab 3010 has a thickness 3015 defined by a top 3020 and a bottom 3025 thereof. The installation device 3000 includes a cylindrical body 3030 having a length 3035 greater than the thickness 3015 of the slab 3010, a first end 3040 configured to be placed adjacent the top 3020 of the slab 3010, and a second end 3045 configured to be placed below the bottom 3025 of the slab 3010. The installation device 3000 also includes an internal cavity 3050 extending longitudinally through the cylindrical body 3030 from the first end 3040 of the cylindrical body 3030 to the second end 3045 of the cylindrical body 3030. The internal cavity 3050 has a first portion 3055 and a second portion 3060, where the first portion 3055 has a first diameter 3065 located at the first end 3040 of the cylindrical body 3030 and the second portion 3060 has a second diameter 3070 that is less than the first diameter 3065. As shown, the internal cavity 3050 of the cylindrical body 3030 is configured to receive the adaptor body 3005; see adaptor body 3005 received therein in FIG. 26.

A cap 3075 can be provided that is configured to seal the first end 3040 of the cylindrical body 3030. The cap 3075 can include a flange 3080 and a projection 3085. The flange 3080 has a diameter 3090 greater than an outer diameter 3095 of the first end 3040 of the cylindrical body 3030. The projection 3085 has a diameter 3100 substantially the same as the first diameter 3065 of the first portion 3055 of the internal cavity 3050, where the projection 3085 is configured to fit within the first portion 3055 of the internal cavity 3050 and seal the first end 3040 of the cylindrical body 3030. The projection 3085 can include one or more o-rings 3087 to facilitate sealing the first end 3040 of the cylindrical body 3030.

The installation device 3000 can also include one or more conduits 3105 providing fluid communication between the second portion 3060 of the internal cavity 3050 and an exterior of the cylindrical body 3030, such as a sub-slab base material 3110. For example, the one or more conduits 3105 can be proximate the second end 3045 of the cylindrical body 3030, where the second end 3045 is configured to be placed below the bottom 3025 of the slab 3010 and into the sub-slab base material 3110.

The cylindrical body 3030 of the installation device 3000 can include a first external surface 3115 having a first diameter 3120 and a second external surface 3125 having a second diameter 3130 that is different than the first diameter 3120. In this way, for example, the change between the first diameter 3120 and the second diameter 3130 can minimize or prevent movement of the cylindrical body 3030 relative to the slab 3010, especially where the slab 3010 is formed around the installation device 3000; e.g., a concrete slab 3010 can be poured around the installation device 3000. The cylindrical body 3030 can also include an external raised portion 3135 having a diameter 3140 greater than the diameters of flanking portions 3145 thereof. The cylindrical body can also include an external recessed portion 3150 having a diameter (e.g., second diameter 3130) less than the diameters (e.g., first diameter 3120 and diameter 3140) of flanking portions thereof. One or more external raised portions 3135 and/or one or more external recessed portions 3150 can minimize or prevent movement of the cylindrical body 3030 relative to the slab 3010. Minimizing or preventing movement of the cylindrical body 3030 relative to the slab 3010 can be important to offset forces applied in disposing the adaptor body 3005 within the installation device 3000, removing the adaptor body 3005 from the installation device 3000, or exchanging the adaptor body 3005 within the installation device 3000 for a similar or different adaptor body 3005. Minimizing or preventing movement of the cylindrical body 3030 relative to the slab 3010 can also maintain a seal between the installation device 3000 and a vapor intrusion barrier 3160.

The installation device 3000 can also be used with a rod 3155 having a length greater than the cylindrical body 3030. The rod 3155 can be configured to be disposed through the internal cavity 3050 of the cylindrical body 3030. As shown in FIG. 25, the rod 3155 can be disposed entirely through the internal cavity 3050, extending from the first end 3040 and extending from the second end 3045, where the rod 3155 extends through the sub-slab base material 3110 and into native soil 3163 below the sub-slab base material 3110. The rod 3155 can be threaded, which can facilitate installation and removal thereof. The rod 3155 can also have a sharp point at one end useful for piercing a vapor intrusion barrier 3160 located between the bottom 3025 of the slab 3010 and the sub-slab base material 3110, as well as for advancing the rod 3155 through the sub-slab base material 3110 and/or the native soil 3163. Likewise, the cylindrical body 3030 of the installation device 3000 can include a pointed, shaped, tapered, and/or threaded portion at or near the second end 3045 to facilitate piercing the vapor intrusion barrier 3160 as well as for advancing the cylindrical body 3030 through the sub-slab base material 3110 and/or the native soil 3163. The internal cavity 3050 extending the length 3035 of the cylindrical body 3030 allows soil gas to flow from underneath the vapor intrusion barrier 3160 through the internal cavity 3050.

FIG. 26 illustrates the installation device 3000 with an adaptor body 3005 received therein. The adaptor body 3005 is similar to the adaptor bodies 1900, 2200 illustrated in FIGS. 19-21 and FIGS. 22-23 and the installation device 3000 can be used with the various embodiments of adaptor bodies described herein. The adaptor body 3005 has a length 3165, a proximal end 3170, and a distal end 3175. The adaptor body 3005 includes a first barbed portion 3180 disposed at the proximal end 3170 of the adaptor body 3005 and a second barbed portion 3185 disposed at the distal end 3175 of the adaptor body 3005. A collar portion 3190 is disposed between the first barbed portion 3180 and the second barbed portion 3185. The adaptor body 3005 has an internal cavity 3195 having an interior surface 3200 that passes through the length 3165 of the adaptor body 3005.

As shown in FIG. 26, the adaptor body 3005 is disposed within the installation device 3000. The first barbed portion 3180 of the adaptor body 3005 can be located within the first portion 3055 of the internal cavity 3050 of the installation device 3000 and the second barbed portion 3185 of the adaptor body 3005 can be located within the second portion 3060 of the internal cavity 3050 of the installation device 3000. A tubular body 3205 can be included to provide a seal between at least a portion of the second barbed portion 3185 of the adaptor body 3005 and the second portion 3060 of the internal cavity 3050 of the installation device 3000.

The adaptor body 3005 can also include a coupling portion 3210 including an internal thread 3215 disposed on the interior surface 3200 and extending longitudinally thereon from the distal end 3175 of the adaptor body 3005. Although not shown in FIG. 26, an extension can be provided for coupling to the adaptor body 3005. The extension can include a length extension and can include extensions such as a fitting extension, filter extension, and/or sieve extension as described herein for extensions 902, 922, 952, 972 shown in FIGS. 14-18. A cover 3220 can be placed over the first end 3040 of the cylindrical body 3030 of the installation device 3000 to cover, protect, and/or control access to the adaptor body 3005 within the installation device 3000.

Various embodiments of the installation device 3000 and various embodiments of the adaptor body 3005 can be used in various ways. For example, a method of installing the installation device 3000 can include placing the rod 3155 into the sub-slab base material 3110, where the rod 3155 has a length greater than the cylindrical body 3030 of the installation device 3000 and the rod 3155 is configured to be disposed through the internal cavity 3050 of the cylindrical body 3030. The cylindrical body 3030 of the installation device 3000 is disposed about the rod 3155, where the rod 3155 is disposed through the internal cavity 3050 of the cylindrical body 3030 and the second end 3045 of the cylindrical body 3030 is disposed into the sub-slab base material 3110. The rod 3155 can then be removed from the sub-slab base material 3110 and the cylindrical body 3030 of the installation device 3000. After removing the rod 3155 from the sub-slab base material 3110 and the cylindrical body 3030 of the installation device 3000, the adaptor body 3005 can be disposed within the installation device 3000, where the adaptor body 3005 can be similar to the adaptor bodies 1900, 2200 illustrated in FIGS. 19-21 and FIGS. 22-23 and the installation device 3000 can be used with the various embodiments of adaptor bodies described herein. The method can further include piercing the vapor intrusion barrier 3160 located at a top of the sub-slab base material 3110 using the rod 3155 as well as marrying the vapor intrusion barrier 3160 to the cylindrical body 3030 of the installation device 3000. In this way, the vapor intrusion barrier 3160 is sealed or substantially sealed with respect to the installation device 3000 so that all or substantially all sub-slab soil gas in the vicinity can pass into/through the internal cavity 3050 of the cylindrical body 3030 of the installation device 3000 and not between the vapor intrusion barrier 3160 and the cylindrical body 3030. Prior to removing the rod, the method can also include sealing the first end 3040 of the cylindrical body 3030 of the installation device 3000 with a cap 3075 and forming a slab 3010 about the installation device 3000, where the first end 3040 of the cylindrical body 3030 of the installation device 3000 is adjacent the top 3020 of the slab 3010 and the second end 3045 of the cylindrical body 3030 of the installation device 3000 is below the bottom 3025 of the slab 3010. Prior to placing the rod 3155 into the sub-slab base material 3110, the method can also include forming a bore through a slab 3010 to the sub-slab base material 3110, where the bore is configured to accommodate the rod 3155 and the cylindrical body 3030 of the installation device 3000 therethrough. Other examples include methods of collecting a gas sample that involve drawing the gas sample through the adaptor body 3005 from a sub-slab base material 3110, where the adaptor body 3005 is disposed within the installation device 3000, the installation device 3000 is disposed within the slab 3010, and the slab 3010 has a thickness 3015 defined by a top 3020 and a bottom 3025 thereof.

Referring to FIG. 27, another method of collecting gas samples is described. The installation device 3000 is provided having a cylindrical body 3030 having a length 3035 and first 3040 and second 3045 ends and an internal cavity 3050 extending longitudinally through the cylindrical body 3030 from the first end 3040 of the cylindrical body 3030 to the second end 3045 of the cylindrical body 3030. The cylindrical body 3030 is placed into a vapor barrier 3160 by piercing the vapor barrier 3160 and the cylindrical body 3030 is sealed to the vapor barrier 3160. A concrete slab 3010 is placed or poured on top of the vapor barrier 3160. An adaptor body 3005 having a first barbed end 3180 and a second barbed end 3185 is inserted into the cylindrical body 3030, where at least a portion of the second barbed end 3185 of the adaptor body 3005 is placed into the internal cavity 3050 of the cylindrical body 3030. At least a portion of the first barbed end 3180 of the adaptor body 3005 is placed into an installation cavity of a handle of an installation tool, as shown and described herein in reference to FIG. 8. The handle is struck on an opposite end of the installation cavity to force the adaptor body 3005 into the cylindrical body 3030 and the installation handle is removed from the first barbed end 3180.

There are various ways to install the installation device 3000 and the adaptor body 3005 in a newly-placed slab, for example, where fresh concrete is to be poured around the installation device 3000. Such an install in new construction can include the following aspects:

1) Check for buried obstacles (e.g., pipes, electrical lines, etc.) prior to proceeding.
2) Locate the desired position (horizontally and vertically) of the top of the installation device.
3) Pierce the vapor intrusion barrier, when present, with a threaded rod of sufficient length to extend slightly above the desired elevation of the finished floor and into the subgrade a sufficient depth to provide support for the installation device. Make sure the rod is perpendicular to the proposed floor surface. Avoid bending the rod, as it may inhibit its removal after the slab concrete has cured. Also avoid damaging the threads on the rod.
4) Dry fit the installation device and trim, or extend the length, and add vent holes as necessary based upon the desired slab thickness.
5) Assemble the installation device and cap by pressing the cap into the top of the installation device. Position the assembly on the threaded rod so that the top of the cap lies flush with the desired elevation of the finished floor. It is important that the position of the installation device be perpendicular to the slab so that a cover used to enclose the installation device (and eventual adaptor body installed therein) meets uniformly with the finished top of the slab or floor.
6) Marry the vapor intrusion barrier to the installation device prior to pouring the concrete slab.
7) After the concrete slab has set, remove the threaded rod and cap and install the adaptor body in the installation device.

There are various ways to install the installation device 3000 and the adaptor body 3005 in a pre-existing slab, for example, where one or more conduits or passageways are cored or bored through pre-existing slab. Such an install in a pre-existing construction can include the following aspects:

1) Check for buried obstacles (e.g., pipes, electrical lines, etc.) prior to proceeding.
2) Prior to installation in an existing slab, a large diameter hole must be cored through the slab to either expose the barrier, or provide access to the base beneath the slab prior to the application of a vapor mitigation barrier or coating. Marry the vapor intrusion barrier or coating to the installation device when placing the installation device within the cored hole through the slab.
3) Locate the desired position (horizontally and vertically) of the top of the adaptor body.
4) Pierce the vapor intrusion barrier (if applicable) with a threaded rod of sufficient length to extend slightly above the elevation of the finished floor and into the sub-slab base material a sufficient depth to provide support for the installation device. Make sure the rod is perpendicular to the proposed floor surface. Avoid bending the rod, as it may inhibit its removal after the concrete has cured. Also avoid damaging the threads on the rod.
5) Dry fit the installation device and trim, or extend the length, and add vent holes as necessary.
6) Assemble the adaptor body and cap by pressing the cap into the top of the installation device. Position the assembly on the threaded rod so that the top of the cap lies flush with the elevation of the finished floor. It is important that the position of the installation device be perpendicular to the slab so that a cover used to enclose the installation device (and eventual adaptor body installed therein) meets uniformly with the finished top of the slab or floor.
7) Marry the vapor intrusion barrier to the installation device to prevent or substantially prevent soil gas from passing between the vapor intrusion barrier and the exterior of the installation device.
8) Remove the threaded rod and cap and install the adaptor body in the installation device.

These and other configurations of the exemplary system components and uses thereof will be evident to those skilled in the art after reading the disclosure provided herein. The invented systems and methods may thus be used to sample sub-slab soil gas with increased efficiency and extensibility, and can further reduce the intrusion of such sampling activities into the day-to-day operations being conducted in any given sampling site.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms, and that neither should be construed to limit the scope of the disclosure. In some example embodiments, well-known processes, well-known device structures, and well-known technologies are not described in detail. Equivalent changes, modifications and variations of some embodiments, materials, compositions and methods can be made within the scope of the present technology, with substantially similar results.

What is claimed is:

1. An installation device for receiving and installing an adaptor body for sampling soil gas under a slab, the slab having a thickness defined by a top and a bottom thereof, the installation device comprising:
   a cylindrical body having a length greater than the thickness of the slab, a first end configured to be placed adjacent the top of the slab, and a second end configured to be placed below the bottom of the slab; and
   an internal cavity extending longitudinally through the cylindrical body from the first end of the cylindrical body to the second end of the cylindrical body, the internal cavity having a first portion and a second portion, the first portion having a first diameter located at the first end of the cylindrical body, the second portion having a second diameter that is less than the first diameter, wherein the internal cavity of the cylindrical body is configured to receive the adaptor body, and wherein an entirety of the first portion and the second portion are disposed below the top of the slab.

2. The installation device of claim 1, wherein the cylindrical body includes a first external surface having a first diameter and a second external surface having a second diameter that is different than the first diameter.

3. The installation device of claim 1, wherein the cylindrical body includes an external raised portion having a diameter greater than the diameters of flanking portions thereof.

4. The installation device of claim 1, wherein the cylindrical body includes an external recessed portion having a diameter less than the diameters of flanking portions thereof.

5. The installation device of claim 1, further comprising a cap configured to seal the first end of the cylindrical body.

6. The installation device of claim 5, wherein the cap includes a flange and a projection, the flange having a diameter greater than an outer diameter of the first end of the cylindrical body, the projection having a diameter substantially the same as the first diameter of the first portion of the internal cavity, the projection configured to fit within the first portion of the internal cavity and seal the first end of the cylindrical body.

7. The installation device of claim 1, further comprising at least one conduit providing fluid communication between the second portion of the internal cavity and an exterior of the cylindrical body.

8. The installation device of claim 7, wherein the at least one conduit is proximate the second end of the cylindrical body.

9. The installation device of claim 1, further comprising a rod having a length greater than the cylindrical body, the rod configured to be disposed through the internal cavity of the cylindrical body.

10. The installation device of claim 9, wherein the rod is threaded.

11. A slab having a thickness defined by a top and a bottom thereof, the slab having an installation device according to claim 1 installed therein, the first end of the cylindrical body placed adjacent the top of the slab and the second end of the cylindrical body placed below the bottom of the slab.

12. The slab of claim 11, wherein the slab is concrete.

13. The slab of claim 11, further comprising a vapor intrusion barrier adjacent the bottom of the slab.

14. The installation device of claim 1, further comprising an adaptor body having a length, a proximal end, and a distal end, the adaptor body including:
a first barbed portion disposed at the proximal end of the adaptor body;
a second barbed portion disposed at the distal end of the adaptor body;
a collar portion disposed between the first barbed portion and the second barbed portion; and
an internal cavity having an interior surface and passing through the length of the adaptor body.

15. The installation device of claim 14, wherein the adaptor body further comprises a coupling portion including an internal thread disposed on the interior surface and extending longitudinally thereon from the distal end of the adaptor body.

16. The installation device of claim 15, further comprising an extension having a length and first and second ends, the extension including:
an internal cavity extending longitudinally through the extension from the first end of the extension to an outlet at the second end of the extension; and
an external thread disposed at the first end adapted for complimentary threaded retention within the coupling portion of the adaptor body.

17. The installation device of claim 14, wherein the adaptor body is disposed within the installation device.

18. The installation device of claim 17, wherein the first barbed portion of the adaptor body is located within the first portion of the internal cavity of the installation device and the second barbed portion of the adaptor body is located within the second portion of the internal cavity of the installation device.

19. The installation device of claim 18, further comprising a tubular body providing a seal between at least a portion of the second barbed portion of the adaptor body and the second portion of the internal cavity of the installation device.

20. A method of installing an installation device according to claim 1, the method comprising:
placing a rod into a sub-slab base material, the rod having a length greater than the cylindrical body of the installation device, the rod configured to be disposed through the internal cavity of the cylindrical body;
disposing the cylindrical body of the installation device about the rod, the rod being disposed through the internal cavity of the cylindrical body, the second end of the cylindrical body disposed into the sub-slab base material; and
removing the rod from the sub-slab base material and the cylindrical body of the installation device.

21. The method of claim 20, wherein after removing the rod from the sub-slab base material and the cylindrical body of the installation device, the method further comprises disposing an adaptor body within the installation device, the adaptor body having a length, a proximal end, and a distal end, the adaptor body including:
a first barbed portion disposed at the proximal end of the adaptor body;
a second barbed portion disposed at the distal end of the adaptor body;
a collar portion disposed between the first barbed portion and the second barbed portion; and
an internal cavity having an interior surface and passing through the length of the adaptor body.

22. The method of claim 20, further comprising:
piercing a vapor intrusion barrier located at a top of the sub-slab base material using the rod; and
marrying the vapor intrusion barrier to the cylindrical body of the installation device.

23. The method of claim 20, wherein prior to removing the rod, the method further comprises:
sealing the first end of the cylindrical body of the installation device with a cap; and
forming a slab about the installation device, the first end of the cylindrical body of the installation device adjacent the top of the slab and the second end of the cylindrical body of the installation device below the bottom of the slab.

24. The method of claim 20, wherein prior to placing the rod into the sub-slab base material, the method further comprises:
forming a bore through a slab to the sub-slab base material, the bore configured to accommodate the rod and cylindrical body of the installation device therethrough.

25. A method of collecting a gas sample comprising:
drawing a gas sample through an adaptor body from a sub-slab base material, the adaptor body disposed within an installation device, the installation device disposed within a slab, the slab having a thickness defined by a top and a bottom thereof;

wherein:

the installation device includes:

a cylindrical body having a length greater than the thickness of the slab, a first end adjacent the top of the slab, and a second end below the bottom of the slab; and an internal cavity extending longitudinally through the cylindrical body from the first end of the cylindrical body to the second end of the cylindrical body, the internal cavity having a first portion and a second portion, the first portion having a first diameter located at the first end of the cylindrical body, the second portion having a second diameter that is less than the first diameter, wherein the internal cavity of the cylindrical body is configured to receive the adaptor body, and wherein an entirety of the first portion and the second portion are disposed below the top of the slab; and the adaptor body includes:

a first barbed portion disposed at the proximal end of the adaptor body;

a second barbed portion disposed at the distal end of the adaptor body;

a collar portion disposed between the first barbed portion and the second barbed portion; and an internal cavity having an interior surface and passing through the length of the adaptor body.

\* \* \* \* \*